US008354246B2

(12) United States Patent
Ebright et al.

(10) Patent No.: US 8,354,246 B2
(45) Date of Patent: Jan. 15, 2013

(54) NON-MCCJ25-RELATED LARIAT-PEPTIDE INHIBITORS OF BACTERIAL RNA POLYMERASE

(75) Inventors: Richard H. Ebright, North Brunswick, NJ (US); Jayanta Mukhopadhyay, Edison, NJ (US); Konstantin Severinov, Piscataway, NJ (US); Ekaterina Semenova, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 12/642,396

(22) Filed: Dec. 18, 2009

(65) Prior Publication Data

US 2011/0201040 A1 Aug. 18, 2011

Related U.S. Application Data

(63) Continuation of application No. 12/281,703, filed as application No. PCT/US2007/006282 on Mar. 13, 2007, now abandoned.

(60) Provisional application No. 60/781,339, filed on Mar. 13, 2006.

(51) Int. Cl.
*C12Q 1/02* (2006.01)

(52) U.S. Cl. ............... 435/29; 435/252.1; 435/252.2; 435/252.8; 435/193; 514/1.1; 514/2.3; 514/2.8; 514/21.1; 514/21.4; 514/21.5

(58) Field of Classification Search .......... 435/29, 435/252.2, 252.5, 252.8, 193; 514/1.1, 2.3, 514/2.8, 21.1, 21.4, 21.5
See application file for complete search history.

(56) References Cited

FOREIGN PATENT DOCUMENTS

| WO | 2004/023093 | 3/2004 |
| WO | 2005/001034 | 1/2005 |

OTHER PUBLICATIONS

Pavlova et al. J. Biol. Chem. (2008) 283(37): 25589-25595.*
Semenova, E., et al., "Structure-Activity of Microcin J25: Distinct Parts of the Threaded Lasso Molecule are Responsible for Interaction with Bacterial RNA Polymerase", Journal of Bacteriology, vol. 187, No. 11, 3859-3863, (Jun. 2005).
Nishio, M., et al., "Siamycins I and II, New Anti-HIV Peptides: I. Fermentation, Isolation, Biological Activity and Initial Characterization", The Journal of Antibiotics, vol. 48, No. 5, 433-434, (1995).
Rosengren, K.J., et al., "Microcin J25 has a Threaded Sidechain-to-Backbone Ring Structure and Not a Head-to-Tail Cyclized Backbone", J.Am.Chem.Soc, vol. 125, No. 41, 12464-12474; (2003).
Rebuffat, S., et al., "Microcin J25, from the Macrocyclic to the Lasso Structure: Implications for Biosynthetic, Evolutionary and Biotechnological Perspectives", Current Protein and Peptide Science, vol. 5, No. 5, 383-391, (2004).
International Search Report for PCT/US2007/006282, dated Aug. 21, 2007.

* cited by examiner

*Primary Examiner* — Susan Hanley
(74) *Attorney, Agent, or Firm* — Davidson, Davidson & Kappel, LLC

(57) ABSTRACT

The invention provides a method of inhibiting a bacterial RNA polymerases. The invention has applications in control of bacterial RNA polymerase activity, control of bacterial gene expression, control of bacterial growth, antibacterial chemistry, and antibacterial therapy.

39 Claims, 5 Drawing Sheets

Figure 1

| | |
|---|---|
| microcin J25 (MccJ25) | GGAGHVPEYFVGIGTPISFYG |
| siamycin I | CLGVGSCNDFAGCGYAIVCFW |
| siamycin II | CLGIGSCNDFAGCGYAVVCFW |
| siamycin III | CLGIGSCNDFAGCGYAIVCFW |
| RES-701-1 | GNWHGTAPDWFFNYYW |
| RES-701-2 | GNWHGTAPDWFFNYY(7-OH-W) |
| RES-701-3 | GNWHGTSPDWFFNYYW |
| RES-701-4 | GNWHGTSPDWFFNYY(7-OH-W) |
| propeptin | GYPWWDYRDLFGGHTFISP |
| anantin | GFIGWGNDIFGHYSGDF |
| lariatin A | GSQLVYREWVGHSNVIKP |
| lariatin B | GSQLVYREWVGHSNVIKGPP |

Figure 4

SEQUENCE LISTING

<160> NUMBER OF SEQ ID NOS: 37

<210> SEQ ID NO 1
<211> LENGTH: 21
<212> TYPE: PRT
<213> ORGANISM: Escheria coli
<220> FEATURE:
<221> NAME/KEY: CHAIN
<222> LOCATION: (1)..(8)
<223> OTHER INFORMATION: Backbone sidechain amide linkage
<220> FEATURE:
<223> OTHER INFORMATION: Microcin J25

<400> SEQUENCE: 1

Gly Gly Ala Gly His Val Pro Glu Tyr Phe Val Gly Ile Gly Thr Pro
1               5                   10                  15

Ile Ser Phe Tyr Gly
            20

<210> SEQ ID NO 2
<211> LENGTH: 15
<212> TYPE: PRT
<213> ORGANISM: Escherichia coli

<400> SEQUENCE: 2

Gln Ile Arg Gln Leu Ala Gly Met Arg Gly Leu Met Ala Arg Lys
1               5                   10                  15

<210> SEQ ID NO 3
<211> LENGTH: 15
<212> TYPE: PRT
<213> ORGANISM: Haemophilus influenzae

<400> SEQUENCE: 3

Gln Ile Arg Gln Leu Ala Gly Met Arg Gly Leu Met Ala Arg Lys
1               5                   10                  15

<210> SEQ ID NO 4
<211> LENGTH: 15
<212> TYPE: PRT
<213> ORGANISM: Vibrio cholerae

<400> SEQUENCE: 4

Gln Ile Arg Gln Leu Ala Gly Met Arg Gly Leu Met Ala Arg Lys
1               5                   10                  15

<210> SEQ ID NO 5
<211> LENGTH: 15
<212> TYPE: PRT
<213> ORGANISM: Pseudomonas aeruginosa

<400> SEQUENCE: 5

Gln Ile Arg Gln Leu Ala Gly Met Arg Gly Leu Met Ala Arg Lys
1               5                   10                  15

<210> SEQ ID NO 6
<211> LENGTH: 15
<212> TYPE: PRT
<213> ORGANISM: Treponema pallidum

<400> SEQUENCE: 6

Gln Ile Arg Gln Leu Ala Gly Met Arg Gly Leu Met Ala Arg Lys
1               5                   10                  15

```
<210> SEQ ID NO 7
<211> LENGTH: 15
<212> TYPE: PRT
<213> ORGANISM: Borrelia burgdorferi

<400> SEQUENCE: 7

Gln Ile Arg Gln Leu Ala Gly Met Arg Gly Leu Met Ala Arg Lys
1               5                   10                  15

<210> SEQ ID NO 8
<211> LENGTH: 15
<212> TYPE: PRT
<213> ORGANISM: Xyella fastidiosa

<400> SEQUENCE: 8

Gln Ile Arg Gln Leu Ala Ala Met Arg Gly Leu Met Ala Arg Lys
1               5                   10                  15

<210> SEQ ID NO 9
<211> LENGTH: 15
<212> TYPE: PRT
<213> ORGANISM: Campylobacter jejuni

<400> SEQUENCE: 9

Gln Ile Ser Gln Leu Ala Ala Met Arg Gly Leu Met Ala Arg Lys
1               5                   10                  15

<210> SEQ ID NO 10
<211> LENGTH: 15
<212> TYPE: PRT
<213> ORGANISM: Neisseria meningitidis

<400> SEQUENCE: 10

Gln Ile Lys Gln Leu Ser Gly Met Arg Gly Leu Met Ala Arg Lys
1               5                   10                  15

<210> SEQ ID NO 11
<211> LENGTH: 15
<212> TYPE: PRT
<213> ORGANISM: Rickettsia prowazekii

<400> SEQUENCE: 11

Gln Ile Lys Gln Leu Gly Gly Met Arg Gly Leu Met Met Arg Lys
1               5                   10                  15

<210> SEQ ID NO 12
<211> LENGTH: 15
<212> TYPE: PRT
<213> ORGANISM: Thermotoga maritima

<400> SEQUENCE: 12

Gln Val Lys Gln Leu Ala Gly Ile Arg Gly Leu Met Ala Arg Lys
1               5                   10                  15

<210> SEQ ID NO 13
<211> LENGTH: 15
<212> TYPE: PRT
<213> ORGANISM: Chlamydia trachomatis

<400> SEQUENCE: 13

Gln Leu Lys Gln Leu Gly Ala Leu Arg Gly Leu Met Ala Arg Lys
1               5                   10                  15

<210> SEQ ID NO 14
<211> LENGTH: 15
<212> TYPE: PRT
```

<213> ORGANISM: Mycoplasma pneumoniae

<400> SEQUENCE: 14

Asn Phe Thr Gln Leu Phe Gly Met Arg Gly Leu Met Ala Arg Lys
1               5                   10                  15

<210> SEQ ID NO 15
<211> LENGTH: 15
<212> TYPE: PRT
<213> ORGANISM: Bacillus subtilis

<400> SEQUENCE: 15

Asn Phe Thr Gln Leu Ala Gly Met Arg Gly Leu Met Ala Arg Lys
1               5                   10                  15

<210> SEQ ID NO 16
<211> LENGTH: 15
<212> TYPE: PRT
<213> ORGANISM: Staphylococcus aureus

<400> SEQUENCE: 16

Asn Phe Thr Gln Leu Ala Gly Met Arg Gly Leu Met Ala Arg Lys
1               5                   10                  15

<210> SEQ ID NO 17
<211> LENGTH: 15
<212> TYPE: PRT
<213> ORGANISM: Mycobacterium tuberculosis

<400> SEQUENCE: 17

Gln Thr Arg Thr Leu Ala Gly Met Lys Gly Leu Val Ala Arg Lys
1               5                   10                  15

<210> SEQ ID NO 18
<211> LENGTH: 15
<212> TYPE: PRT
<213> ORGANISM: Synechocystis sp

<400> SEQUENCE: 18

Gln Val Arg Gln Leu Val Gly Met Arg Gly Leu Met Ala Arg Lys
1               5                   10                  15

<210> SEQ ID NO 19
<211> LENGTH: 15
<212> TYPE: PRT
<213> ORGANISM: Aquifex aeolicus

<400> SEQUENCE: 19

Gln Ile Arg Gln Leu Ala Gly Met Arg Gly Leu Met Ala Arg Lys
1               5                   10                  15

<210> SEQ ID NO 20
<211> LENGTH: 15
<212> TYPE: PRT
<213> ORGANISM: Deinococcus radiodurans

<400> SEQUENCE: 20

Gln Ile Arg Gln Leu Ala Gly Met Arg Gly Leu Met Ala Arg Lys
1               5                   10                  15

<210> SEQ ID NO 21
<211> LENGTH: 15
<212> TYPE: PRT
<213> ORGANISM: Thermus thermophilus

<400> SEQUENCE: 21

```
Gln Ile Arg Gln Leu Cys Gly Leu Arg Gly Leu Met Ala Arg Lys
1               5                   10                  15
```

<210> SEQ ID NO 22
<211> LENGTH: 15
<212> TYPE: PRT
<213> ORGANISM: Thermus aquaticus

<400> SEQUENCE: 22

```
Gln Ile Arg Gln Leu Cys Gly Met Arg Gly Leu Met Ala Arg Lys
1               5                   10                  15
```

<210> SEQ ID NO 23
<211> LENGTH: 15
<212> TYPE: PRT
<213> ORGANISM: Homo sapiens
<220> FEATURE:
<223> OTHER INFORMATION: Human RNAP I

<400> SEQUENCE: 23

```
Asn Thr Met Gln Ile Ser Cys Leu Leu Gly Gln Ile Gly Arg Glu
1               5                   10                  15
```

<210> SEQ ID NO 24
<211> LENGTH: 15
<212> TYPE: PRT
<213> ORGANISM: Homo sapiens
<220> FEATURE:
<223> OTHER INFORMATION: Human RNAP II

<400> SEQUENCE: 24

```
Asn Ile Ser Gln Val Ile Ala Val Val Gly Gln Gln Gly Arg Glu
1               5                   10                  15
```

<210> SEQ ID NO 25
<211> LENGTH: 15
<212> TYPE: PRT
<213> ORGANISM: Homo sapiens
<220> FEATURE:
<223> OTHER INFORMATION: Human RNAP III

<400> SEQUENCE: 25

```
Asn Ile Ser Gln Met Ile Ala Cys Val Gly Gln Gln Gly Arg Glu
1               5                   10                  15
```

<210> SEQ ID NO 26
<211> LENGTH: 21
<212> TYPE: PRT
<213> ORGANISM: Escherichia coli
<220> FEATURE:
<221> NAME/KEY: CHAIN
<222> LOCATION: (1)..(8)
<223> OTHER INFORMATION: Backbone sidechain amide linkage

<400> SEQUENCE: 26

```
Gly Gly Ala Gly His Val Pro Glu Tyr Phe Val Gly Ile Gly Thr Pro
1               5                   10                  15

Ile Ser Phe Tyr Gly
            20
```

<210> SEQ ID NO 27
<211> LENGTH: 21
<212> TYPE: PRT
<213> ORGANISM: Streptomyces sp.
<220> FEATURE:
<221> NAME/KEY: CHAIN
<222> LOCATION: (1)..(9)

```
<223> OTHER INFORMATION: Backbone sidechain amide linkage
<220> FEATURE:
<221> NAME/KEY: CHAIN
<222> LOCATION: (1)..(13)
<223> OTHER INFORMATION: sidechain-sidechain disulfide linkage
<220> FEATURE:
<221> NAME/KEY: CHAIN
<222> LOCATION: (7)..(19)
<223> OTHER INFORMATION: sidechain-sidechain disulfide linkage

<400> SEQUENCE: 27

Cys Leu Gly Val Gly Ser Cys Asn Asp Phe Ala Gly Cys Gly Tyr Ala
1               5                   10                  15

Ile Val Cys Phe Trp
            20

<210> SEQ ID NO 28
<211> LENGTH: 21
<212> TYPE: PRT
<213> ORGANISM: Streptomyces sp.
<220> FEATURE:
<221> NAME/KEY: CHAIN
<222> LOCATION: (1)..(9)
<223> OTHER INFORMATION: Backbone sidechain amide linkage
<220> FEATURE:
<221> NAME/KEY: CHAIN
<222> LOCATION: (1)..(13)
<223> OTHER INFORMATION: sidechain-sidechain disulfide linkage
<220> FEATURE:
<221> NAME/KEY: CHAIN
<222> LOCATION: (7)..(19)
<223> OTHER INFORMATION: sidechain-sidechain disulfide linkage

<400> SEQUENCE: 28

Cys Leu Gly Ile Gly Ser Cys Asn Asp Phe Ala Gly Cys Gly Tyr Ala
1               5                   10                  15

Ile Val Cys Phe Trp
            20

<210> SEQ ID NO 29
<211> LENGTH: 21
<212> TYPE: PRT
<213> ORGANISM: Streptomyces griseoflavus
<220> FEATURE:
<221> NAME/KEY: CHAIN
<222> LOCATION: (1)..(9)
<223> OTHER INFORMATION: Backbone sidechain amide linkage
<220> FEATURE:
<221> NAME/KEY: CHAIN
<222> LOCATION: (1)..(13)
<223> OTHER INFORMATION: sidechain-sidechain disulfide linkage
<220> FEATURE:
<221> NAME/KEY: CHAIN
<222> LOCATION: (7)..(19)
<223> OTHER INFORMATION: sidechain-sidechain disulfide linkage

<400> SEQUENCE: 29

Cys Leu Gly Ile Gly Ser Cys Asn Asp Phe Ala Gly Cys Gly Tyr Ala
1               5                   10                  15

Val Val Cys Phe Trp
            20

<210> SEQ ID NO 30
<211> LENGTH: 16
<212> TYPE: PRT
<213> ORGANISM: Streptomyces sp.
<220> FEATURE:
<221> NAME/KEY: CHAIN
<222> LOCATION: (1)..(9)
<223> OTHER INFORMATION: Backbone sidechain amide linkage
```

-continued

```
<400> SEQUENCE: 30

Gly Asn Trp His Gly Thr Ala Pro Asp Trp Phe Phe Asn Tyr Tyr Trp
1               5                   10                  15

<210> SEQ ID NO 31
<211> LENGTH: 16
<212> TYPE: PRT
<213> ORGANISM: Streptomyces sp.
<220> FEATURE:
<221> NAME/KEY: CHAIN
<222> LOCATION: (1)..(9)
<223> OTHER INFORMATION: Backbone sidechain amide linkage
<220> FEATURE:
<221> NAME/KEY: modified_base
<222> LOCATION: 16
<223> OTHER INFORMATION: Xaa = 7-hydroxytryptophan

<400> SEQUENCE: 31

Gly Asn Trp His Gly Thr Ala Pro Asp Trp Phe Phe Asn Tyr Tyr Xaa
1               5                   10                  15

<210> SEQ ID NO 32
<211> LENGTH: 16
<212> TYPE: PRT
<213> ORGANISM: Streptomyces sp.
<220> FEATURE:
<221> NAME/KEY: CHAIN
<222> LOCATION: (1)..(9)
<223> OTHER INFORMATION: Streptomyces sp.

<400> SEQUENCE: 32

Gly Asn Trp His Gly Thr Ser Pro Asp Trp Phe Phe Asn Tyr Tyr Trp
1               5                   10                  15

<210> SEQ ID NO 33
<211> LENGTH: 16
<212> TYPE: PRT
<213> ORGANISM: Streptomyces sp.
<220> FEATURE:
<221> NAME/KEY: CHAIN
<222> LOCATION: (1)..(9)
<223> OTHER INFORMATION: Backbone sidechain amide linkage
<220> FEATURE:
<221> NAME/KEY: modified_base
<222> LOCATION: 16
<223> OTHER INFORMATION: Xaa = 7-hydroxytryptophan

<400> SEQUENCE: 33

Gly Asn Trp His Gly Thr Ser Pro Asp Trp Phe Phe Asn Tyr Tyr Xaa
1               5                   10                  15

<210> SEQ ID NO 34
<211> LENGTH: 19
<212> TYPE: PRT
<213> ORGANISM: Microbispora sp.
<220> FEATURE:
<221> NAME/KEY: CHAIN
<222> LOCATION: (1)..(9)
<223> OTHER INFORMATION: Backbone sidechain amide linkage

<400> SEQUENCE: 34

Gly Tyr Pro Trp Trp Asp Tyr Arg Asp Leu Phe Gly Gly His Thr Phe
1               5                   10                  15

Ile Ser Pro

<210> SEQ ID NO 35
<211> LENGTH: 17
<212> TYPE: PRT
<213> ORGANISM: Streptomyces coerulescens
```

```
<220> FEATURE:
<221> NAME/KEY: CHAIN
<222> LOCATION: (1)..(8)
<223> OTHER INFORMATION: Backbone sidechain amide linkage

<400> SEQUENCE: 35

Gly Phe Ile Gly Trp Gly Asn Asp Ile Phe Gly His Tyr Ser Gly Asp
1               5                   10                  15

Phe

<210> SEQ ID NO 36
<211> LENGTH: 18
<212> TYPE: PRT
<213> ORGANISM: Rhodococcus jostii
<220> FEATURE:
<223> OTHER INFORMATION: lariatin A

<400> SEQUENCE: 36

Gly Ser Gln Leu Val Tyr Arg Glu Trp Val Gly His Ser Asn Val Ile
1               5                   10                  15

Lys Pro

<210> SEQ ID NO 37
<211> LENGTH: 20
<212> TYPE: PRT
<213> ORGANISM: Rhodococcus jostii
<220> FEATURE:
<221> NAME/KEY: CHAIN
<222> LOCATION: (1)..(8)
<223> OTHER INFORMATION: Backbone sidechain amide linkage

<400> SEQUENCE: 37

Gly Ser Gln Leu Val Tyr Arg Glu Trp Val Gly His Ser Asn Val Ile
1               5                   10                  15

Lys Gly Pro Pro
            20
```

NON-MCCJ25-RELATED LARIAT-PEPTIDE INHIBITORS OF BACTERIAL RNA POLYMERASE

CROSS-REFERENCE TO RELATED APPLICATIONS

This application is a Continuation of U.S. patent application Ser. No. 12/281,703, filed Sep. 4, 2008, now abandoned, which is the National Stage of International Application No. PCT/US2007/006282, filed Mar. 13, 2007, which claims the benefit of U.S. provisional application No. 60/781,339, filed Mar. 13, 2006, the entire contents of which are incorporated herein by reference.

GOVERNMENT SUPPORT

This invention was supported by U.S. Government funds (NIH-R01-GM41376). Therefore, the Government may have rights to this invention.

FIELD OF THE INVENTION

This invention relates to methods for inhibiting bacterial RNA polymerases.

BACKGROUND ART

RNA Polymerase

Bacterial infections remain among the most common and deadly causes of human disease. Infectious diseases are the third leading cause of death in the United States and the leading cause of death worldwide (Binder et al. (1999) *Science* 284, 1311-1313). Multi-drug-resistant bacteria now cause infections that pose a grave and growing threat to public health. It has been shown that bacterial pathogens can acquire resistance to first-line and even second-line antibiotics (Stuart B. Levy, The Challenge of Antibiotic Resistance, in Scientific American, 46-53 (March, 1998); Walsh, C. (2000) *Nature* 406, 775-781; Schluger, N. (2000) *Int. J. Tuberculosis Lung Disease* 4, S71-S75; Raviglione et al., (2001) *Ann. NY Acad. Sci.* 953, 88-97). New approaches to drug development are necessary to combat the ever-increasing number of antibiotic-resistant pathogens.

RNA polymerase (RNAP) is the molecular machine responsible for transcription and is the target, directly or indirectly, of most regulation of gene expression (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Murakami & Darst (2003) *Curr. Opin. Structl. Biol.* 13, 31-39; Borukhov & Nudler (2003) *Curr. Opin. Microbiol.* 6, 93-100; Landick, R. (2001) *Cell* 105, 567-570; Korzheva & Mustaev (2001) *Curr. Opin. Microbiol.* 4, 119-125; Armache, et al. (2005) *Curr. Opin. Structl. Biol.* 15, 197-203; Woychik & Hampsey (2002); *Cell* 108, 453-463; Asturias, F. (2004) *Curr. Opin. Genet Dev.* 14, 121-129; Cramer, P. (2004) *Curr. Opin. Genet. Dev.* 14, 218-226; Geiduschek & Kassayetis (2001) *J. Mol. Biol.* 310, 1-26). Bacterial RNAP core enzyme has a molecular mass of ~380,000 Da and consists of one β' subunit, one β subunit, two α subunits, and one ω subunit; bacterial RNAP holoenzyme has a molecular mass of ~450,000 Da and consists of bacterial RNAP core enzyme in complex with the transcription initiation factor σ (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Murakami & Darst (2003) *Curr. Opin. Structl. Biol.* 13, 31-39; Borukhov & Nudler (2003) *Curr. Opin. Microbiol.* 6, 93-100). Bacterial RNAP core subunit sequences from Gram-negative bacterial species, Gram-postive bacterial species, and *Thermococcus-Deinococcus*-clade bacterial species exhibit moderate amino acid sequence conservation (Ebright, R. (2000) *J. Mol. Biol.* 304, 687-698; Darst, S. (2001) *Curr. Opin. Structl. Biol.* 11, 155-162; Iyer, et al. (2004) *Gene* 335, 73-88). Eukaryotic RNAP I, RNAP II, and RNAP III contain counterparts of all bacterial RNAP core subunits, but eukaryotic-subunit sequences and bacterial-subunit sequences exhibit only limited amino acid sequence conservation (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97).

Crystallographic structures have been determined for bacterial RNAP and eukaryotic RNAP II (Zhang et al., (1999) *Cell* 98, 811-824; Cramer et al., (2000) *Science* 288, 640-649; Naryshkin et al., (2000) *Cell* 101, 601-611; Kim et al., (2000) *Science* 288, 1418-1421; Korzheva et al., (2000) *Science* 289, 619-625; Ebright, R. (2000) *J. Mol. Biol.* 304, 687-689; Cramer et al., (2001) *Science* 292, 1863-1876; Gnatt et al., (2001) *Science* 292, 1876-1882; Mekler et al., (2002) *Cell* 108, 599-614; Murakami et al., (2002) *Science* 296, 1280-1284; Murakami et al., (2002) *Science* 296, 1285-1290; Vassylyev et al., (2002) *Nature* 417, 712-719; Bushnell et al., (2004) *Science* 303, 983-988; Westover et al., (2004) *Science* 303, 1014-1016; Armache, et al., (2003) *Proc. Natl. Acad. Sci. USA* 100, 6964-6968). Moreover, cryo-EM structures have been determined for bacterial RNAP and eukaryotic RNAP I (Opalka, et al. (2000) *Proc. Natl. Acad. ScL USA* 97, 617-622; Darst, et al. (2002) *Proc. Natl. Acad. Sci. USA* 99, 4296-4301; DeCarlo, et al. (2003) *J. Mol. Biol.* 329, 891-902).

Structures also have been determined for RNAP complexes with nucleic acids, nucleotides and inhibitors (Campbell, et al. (2001) *Cell* 104, 901-912; Artsimovitch, et al. (2005) *Cell* 122, 351-363; Campbell, et al. (2005) *EMBO J.* 24, 674-682; Artsimovitch, et al. (2004) *Cell* 117, 299-310; Tuske, et al. (2005) *Cell* 122, 541-522; Temiaov, et al. (2005) *Mol. Cell* 19, 655-666; Vassulyev, et al. (2005) *Nature Structl. Biol.* 12, 1086-1093; Gnatt, et al. (2001) *Science* 292, 1876-1882; Westover, et al. (2004a) *Science* 303, 1014-1016; Westover, et al. (2004b) *Cell* 119, 481-489; Ketenberger, et al. (2004) *Mol. Cell* 16, 955-965; Bushnell, et al. (2002) *Proc. Natl. Acad. Sci. USA.* 99, 1218-1222; Kettenberger, et al. (2005) *Natl. Structl. Mol. Biol.* 13, 44-48).

The structures reveal that RNAP-bacterial or eukaryotic—has a shape reminiscent of a crab claw. The two "pincers" of the "claw" define the active-center cleft that can accommodate a double-stranded nucleic acid-and which has the active-center $Mg^{2+}$ at its base. The largest subunit (β' in bacterial RNAP) makes up one pincer, termed the "clamp," and part of the base of the active-center cleft. The second-largest subunit (β in bacterial RNAP) makes up the other pincer and part of the base of the active-center cleft.

Based on crystallographic structures for bacterial RNAP and eukaryotic RNAP biophysical results, and biochemical results, models have been proposed for the structures of transcription initiation and elongation complexes (Gnatt et al., (2001) *Science* 292, 1876-1882; Ebright, R. (2000) *J. Mol. Biol.* 304, 687-689; Naryshkin et al., (2000 *Cell* 101, 601-611; Kim et al., (2000) *Science* 288, 1418-1421; Korzheva et al., (2000) *Science* 289, 619-625; and Mekler et al., (2002) *Cell* 108:599-614).

Bacterial RNAP is a proven target for antibacterial therapy (Chopra, et al. (2002) *J. Appl. Microbiol.* 92, 4S-15S; Darst, S. (2004) *Trends Biochem. Sci.* 29, 159-162). The suitability of bacterial RNAP as a target for antibacterial therapy follows from the fact that bacterial RNAP is an essential enzyme (permitting efficacy), the fact that bacterial RNAP subunit sequences are conserved (providing a basis for broad-spectrum activity), and the fact that bacterial RNAP subunit sequences are only weakly conserved in eukaryotic RNAP I, RNAP II, and RNAP III (providing a basis for therapeutic selectivity).

The rifamycin antibacterial agents—notably rifampicin, rifapentine, and rifabutin—function by binding to and inhibiting bacterial RNAP (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins bind to a site on bacterial RNAP adjacent to the RNAP active center and sterically and/or allosterically prevent extension of RNA chains beyond a length of 2-3 nt (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363).

The rifamycins are in current clinical use in treatment of Gram-negative and 1.0 Gram-positive bacterial infections (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins are of particular importance in treatment of tuberculosis; the rifamycins are first-line anti-tuberculosis agents and are the only anti-tuberculosis agents able rapidly to clear infection and prevent relapse (Mitchison, D. (2000) *Int. J. Tuberc. Lung Dis.* 4, 796-806). The rifamycins also are of importance in treatment of bacterial infections relevant to biowarfare or bioterrorism; combination therapy with ciprofloxacin, clindamycin, and rifampicin was successful in treatment of inhalational anthrax following the 2001 anthrax attacks (Mayer, et al. (2001) *JAMA* 286, 2549-2553), and combination therapy with ciprofloxacin and rifampicin, or doxycycline with rifampicin, is recommended for treatment of future cases of inhalational anthrax (Centers for Disease Control and Prevention (2001) *JAMA* 286, 2226-2232).

The clinical utility of the rifamycin antibacterial agents is threatened by the existence of bacterial strains resistant to known rifamycins (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). Resistance to rifamycins typically involves substitution of residues in or immediately adjacent to the rifamycin binding site on bacterial RNAP—i.e., substitutions that directly decrease binding or function of rifamycins. A significant and increasing percentage of cases of tuberculosis are resistant to rifampicin (1.4% of new cases, 8.7% of previously treated cases, and 100% of cases designated multidrug-resistant, in 1999-2002; Schluger, N. (2000) *Int. J. Tuberc. Lung Dis.* 4, S71-S75; Raviglione, et al. (2001) *Ann. N.Y. Acad. Sci.* 953, 88-97; Zumia, et al. (2001) *Lancet Infect. Dis.* 1, 199-202; Dye, et al. (2002) *J. Infect. Dis.* 185, 1197-1202; WHO/IUATLD (2003) *Anti-tuberculosis drug resistance in the world: third global report* (WHO, Geneva)). Strains of bacterial bioweapons agents resistant to rifampicin can be, and have been, constructed (Lebedeva, et al. (1991) *Antibiot. Khimioter.* 36, 19-22; Pomerantsev, et al. (1993) *Antibiot. Khimioter.* 38, 34-38; Volger, et al. (2002) *Antimicrob. Agents Chemother.* 46, 511-513; Marianelli, et al. (204) *J. Clin. Microbiol.* 42, 5439-5443).

In view of the public-health threat posed by rifamycin-resistant bacterial infections, there is an urgent need for new antibacterial agents that (i) target bacterial RNAP (and thus have the same biochemical effects as rifamycins), but that (ii) target sites within bacterial RNAP distinct from the rifamycin binding site (and thus do not show cross-resistance with rifamycins). (See Chopra, et al. (2002) *J. Appl. Microbiol.* 92, 4S-15S; Darst, S (2004) *Trends Biochem. Sci.* 29, 159-162.)

RNA Polymerase Secondary Channel

Crystallographic structures have been determined for bacterial RNAP and eukaryotic RNAP II (Zhang et al., (1999) *Cell* 98, 811-824; Cramer et al., (2000) *Science* 288, 640-649; Cramer et al., (2001) *Science* 292, 1863-1876; Gnatt et al., (2001 *Science* 292, 1876-1882; and Ebright, R. (2000) *J. Mol. Biol.* 304, 687-689), and, based on the crystallographic structures, biophysical results, and biochemical results, models have been proposed for the structures of transcription initiation and elongation complexes (Gnatt et al., (2001 *Science* 292, 1876-1882; Ebright, R. (2000) *J. Mol. Biol.* 304, 687-689; Naryshkin et al., (2000 *Cell* 101, 601-611; Kim et al., (2000) *Science* 288, 1418-1421; Korzheva et al., (2000) *Science* 289, 619-625; and Mekler et al., (2002) *Cell* 108:599-614).

The models for the transcription elongation complex imply that nucleic acids completely fill the active-center cleft of RNAP, and thus the only route by which incoming nucleoside-triphosphate substrates ("NTPs") can access the active center is through a ~25 Å long, ~10 Å wide tunnel—the "secondary channel," "pore," "nucleotide-uptake channel," or "nucleotide-entrance channel,"—that bores through the floor of the active-center cleft of RNAP and extends to the exterior surface of RNAP opposite the active-center cleft (Gnatt et al., (2001) *Science* 292, 1876-1882; Ebright, R. (2000) *J. Mol. Biol.* 304, 687-689; and Korzheva et al., (2000) *Science* 289, 619-625).

The models for the transcription elongation complex imply that the RNAP secondary channel mediates multiple biochemical activities important for function of RNAP, including: uptake of NTPs, release of pyrophosphate product, release of abortive-RNA and edited-RNA products, interaction with RNA product during transcriptional pausing, interaction with RNA product during transcriptional arrest, interaction with RNA product during editing, and interaction with the elongation factors GreA and GreB.

Physically blocking the RNAP secondary channel with a small molecule can inhibit one or more of these activities and thereby can inhibit function of RNAP (WO 2004/023093; Mukhopadhyay et al. (2004) *Mol. Cell* 14, 739-751; Adelman et al. (2004) *Mol. Cell* 14, 753-762). For example, physically blocking the RNAP secondary channel with a small molecule can prevent uptake of NTPs by RNAP and thus can prevent transcription (WO 2004/023093; Mukhopadhyay et al. (2004) *Mol. Cell* 14, 739-751; Adelman et al. (2004) *Mol. Cell* 14, 753-762).

A region within the RNAP secondary channel—a region that comprises amino acids 736-747 and 779-781 of the RNAP β' subunit in RNAP from *Escherichia coli*—is a useful target for compounds that inhibit transcription, including, by way of example, the lariat peptide microcin J25 (MccJ25) and derivatives thereof (WO 2004/023093; FIG. 1). This region includes residues that are conserved in RNAP from bacterial species, but that are not conserved, and indeed are radically different, in RNAP from eukaryotic species (FIG. 1). This region forms a ~5 Å shallow pocket within the wall of the RNAP secondary channel (FIG. 2). A compound that binds to this region of a bacterial RNAP can physically block the secondary channel of a bacterial RNAP, can prevent uptake of NTPs by a bacterial RNAP, can inhibit bacterial transcription, can inhibit bacterial gene expression, and can inhibit bacterial growth.

The secondary-channel region referred to above in RNAP from *Escherichia coli* is similar in amino acid sequence in RNAP from other species of bacteria and is called herein the "bacterial RNAP homologous secondary channel amino acid sequence" (FIG. 1). (For example, amino acid residues 736-747 and 779-781 of the β' subunit of RNAP from *Escherichia coli* are similar to amino acid residues 740-751 and 783-785 of the β' subunit of RNAP from *Bacillus subtilis* (FIG. 1). Thus, a molecule that binds to this region and inhibits an activity associated with the secondary channel in RNAP from *Escherichia coli* also may bind to this region and inhibit an activity associated with the secondary channel in RNAP from other species of bacteria. Therefore, molecules found to have antibacterial activity (through binding to this region and inhibiting an activity associated with the secondary channel) against *Escherichia coli* also may be found to have antibacterial activity against other species of bacteria.

In contrast, the secondary-channel region referred to above differs radically in amino acid sequence between bacterial RNAP and eukaryotic RNAP, including human RNAP I, human RNAP II, and human RNAP III (FIG. 1). This allows for identification of molecules that bind, in a secondary-channel-region-dependent fashion, to a bacterial RNAP, but that do not bind, or that bind substantially less well, to a eukaryotic RNAP. This also allows for identification of molecules that inhibit, in a secondary-channel region-dependent fashion, an activity of a bacterial RNAP, but that do not inhibit, or that inhibit substantially less well, an activity of a eukaryotic RNAP. This differentiation is important, because it permits the identification of bacterial-RNAP-selective binding molecules and bacteria-selective inhibitors.

In the three-dimensional structure of a bacterial RNAP, the secondary-channel region referred to above is located near to, but does not overlap, the rifamycin binding site (FIG. 3). The distance between the center of the secondary-channel region referred to above and the center of the rifamycin binding pocket is ~25 Å.

The invention provides, by way of example only, a bacterial RNAP homologous secondary channel amino acid sequence corresponding to, and alignable with, residues 736-747 and 779-781 of the β' subunit of RNAP from *Escherichia coli*, as well as with corresponding residues of the β' subunit of *Bacillus subtilis, Haemophilus influenzae, Vibrio cholerae, Pseudomonas aeruginosa, Treponema pallidum, Borrelia burgdorferi, Xyella fastidiosa, Campylobacter jejuni, Neisseria meningitidis, Rickettsia prowazekii, Thermotoga maritima, Chlamydia trachomatis, Mycoplasma pneumoniae, Staphylococcus aureus, Mycobacterium tuberculosis, Synechocystis* sp., *Aquifex aeolicus, Deinococcus radiodurans, Thermus thermophilus*, and *Thermus aquaticus*.

Ligands that bind to the secondary channel of, and inhibit an activity of, a bacterial RNAP are known in the art. Such ligands include, for example, the lariat-peptide microcin J25 (MccJ25)(WO 2004/023093; Mukhopadhyay et al. (2004) *Mol. Cell* 14, 739-751; Adelman, et al. (2004) *Mol. Cell* 14, 753-762; Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483), substituted derivatives of the lariat-peptide MccJ25 (WO 2004/023093; U.S. application Ser. No. 11/371,736, filed Mar. 9, 2006; Mukhopadhyay, et al. (2004) *Mol. Cell* 14, 739-751), and minimized derivatives of lariat-peptide MccJ25 (WO2005/024040; Semenova, et al. (2005) *J. Bacteria* 187:3859-3863). The references cited above are incorporated herein in their entirety.

Lariat-Peptide MccJ25

The antibacterial peptide microcin J25 (MccJ25) inhibits bacterial RNAP by binding within, and obstructing, the secondary channel of bacterial RNAP (WO 2004/023093; Mukhopadhyay et al. (2004) Mol. Cell 14, 739-751; Adelman, et al. (2004) *Mol. Cell* 14, 753-762). MccJ25 has the sequence (Sequence ID NO. 1): $Gly_1$-$Gly_2$-$Ala_3$-$Gly_4$-$His_5$-$Pro_6$-$Val_7$-$Glu_8$-$Tyr_9$-$Phe_{10}$-$Val_{11}$-$Gly_{12}$-$Ile_{13}$-$Gly_{14}$-$Thr_{15}$-$Pro_{16}$-$Ile_{17}$-$Ser_{18}$-$Phe_{19}$-$Tyr_{20}$-$Gly_{21}$ cyclic(8→1) peptide (Bayro, et at. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483; FIG. 4, line 1).

MccJ25 has an unusual "lariat-peptide" covalent structure (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483; FIG. 4, line 1). MccJ25 is 21 amino acids in length and consists of an 8-residue cyclic segment—with a backbone-sidechain amide linkage between the backbone nitrogen atom of residue $Gly_1$ and the side-chain carboxyl group of $Glu_8$—followed by a 13-residue linear segment.

MccJ25 further has an unusual "lariat-protoknot" three-dimensional structure (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483; FIG. 5). In the three-dimensional structure of MccJ25, the linear segment of the lariat loops back and penetrates and threads through the cycle of the lariat, essentially as a thread through the eye of a needle. The linear segment is irreversibly locked in place and trapped within the cycle by steric constraints imposed by the aromatic sidechains of $Phe_{19}$ and $Tyr_{20}$, which bracket the cycle, with the aromatic sidechain of $Phe_{19}$ being on located on one face of the cycle and the aromatic sidechain of $Tyr_{20}$ being located on the other face of the cycle.

The lariat-peptide/lariat-protoknot structure of MccJ25, with irreversible trapping of the linear segment of the lariat within the cycle of the lariat, results in exceptional resistance to denaturation (complete resistance to tested thermal and chemical denaturants; Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483) and exceptional resistance to proteolysis (complete resistance to tested mesophilic endo- and exopeptidease; Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483).

The lariat-peptide/lariat-protoknot structure of MccJ25 is generated by a MccJ25-specific biosynthetic system. MccJ25 is produced by bacterial strains harboring a plasmid-borne lariat-peptide/lariat-protoknot biosynthetic cassette, consisting of a gene for MccJ25 precursor, two genes for factors that process McJ25 precursor into mature MccJ25, and one gene for a factor that exports MccJ25 from the cell (Solbiati, et al. (1999) *J. Bacteriol.* 181, 2659-2662). The gene names and functions are as follows:

mcjA; encodes the MccJ25 precursor (McjA)
mcjB; encodes a MccJ25 processing factor (McjB)
mcjB; encodes a MccJ25 processing factor (McjC)
mcjD; encodes a MccJ25 export factor (McjD)

The MccJ25 precursor is a 58-residue peptide consisting of a 37-residue N-terminal pro-sequence (residues numbered as −37 to −1) and a 21-residue C-terminal segment having the same amino acid sequence as mature MccJ25 (residues numbered as 1 to 21) (Solbiati, et al. (1999) *J. Bacteriol.* 181, 2659-2662).

Processing of the MccJ25 precursor to yield mature MccJ25 entails two reactions: (1) cleavage of the backbone-backbone amide linkage between residue −1 and residue 1, resulting in removal of the 37-residue N-terminal pro-sequence; and (2) formation of a backbone-sidechain amide linkage between the backbone nitrogen atom of residue 1 and the sidechain carboxyl of residue 8, resulting in cyclization of residues 1-8 and entrapment of residues 9-21 (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483). The MccJ25 processing factor McjC exhibits amino acid sequence similarity to amidotransferases of the Asn-synthase/Gln-hydrolase class, which catalyze transfer of ammonia or an amine from an amide donor to a carboxyl acceptor (Bayro, et al. (2003) *J. Am. Chem. Soc.* 125, 12382-12383). It has been proposed that McjC participates in both reactions in processing of the MccJ25 precursor to yield mature MccJ25, acting on pre-folded MccJ25 precursor to catalyze transfer of the backbone nitrogen atom, also known as the α-amino group, of residue 1 from the backbone amide linkage between residue −1 and residue 1 to the sidechain carboxyl of residue 8 (Bayro, et al. (2003) *J. Am. Chem. Soc.* 125, 12382-12383).

It has not been possible to date to re-create the lariat-peptide/lariat-protoknot structure of MccJ25 without use of the above-described MccJ25-specific biosynthetic system. Attempted chemical synthesis of MccJ25 yields a product having a lariat-peptide covalent structure but not having a lariat-protoknot three-dimensional structure (i.e., not having the linear segment of the lariat looped back and penetrating and threading through the cyclic segment of the lariat; the resulting material exhibits no detectable biological activity (Rosengren, et al. (2003) *J. Am. Chem. Soc.* 125, 12464-12474; Wilson, et al. (2003) *J. Am. Chem. Soc.* 125, 12475-12483). Chemical synthesis of a linear analog of MccJ25 yields a product having neither a lariat-peptide covalent structure nor a lariat-protoknot structure; the resulting material exhibits no detectable biological activity (Rosengren, et al. (2003) *J. Am. Chem. Soc.* 125, 12464-12474; Wilson, et al. (2003) *J. Am. Chem. Soc.* 125, 12475-12483). Production of a recombinant linear analog of MccJ25, by use of a nucleic acid sequence encoding the linear analog of MccJ25 likewise yields a product having neither a lariat-peptide covalent structure nor a lariat-protoknot structure and exhibiting no detectable biological activity.

The MccJ25 lariat-peptide/lariat-protoknot biosynthetic cassette is organized as a gene cluster, with gene order mcjA, mcjB, mcjC, mcjD (Solbiati, et al. (1996) *J. Bacteriol.* 178, 3661-3663; Solbiati, et al. (1999) *J. Bacteriol.* 181, 2659-2662). The size of the MccJ25 lariat-peptide/lariat-protoknot biosynthetic cassette is ~4,500 bp.

The MccJ25 lariat-peptide/lariat-protoknot biosynthetic cassette can be expressed in an original, naturally occurring, Mcc25-producer strain, resulting in MccJ25 production (Solbiati, et al. (1996) *J. Bacteriol.* 178, 3661-3663; Solbiati, et al. (1999) *J. Bacteriol.* 181, 2659-2662).

The MccJ25 lariat-peptide/lariat-protoknot biosynthetic cassette also can be introduced into, and expressed in, a surrogate host strain, resulting in surrogate-host MccJ25 production (Solbiati, et al. (1999) *J. Bacteriol.* 181, 2659-2662; Blond, et al. (1999) *Eur. J. Biochem.* 259, 747-755).

Because the nucleotide sequence of the mcjA gene determines the amino acid sequence of the MccJ25 precursor, and because, in MccJ25 biosynthesis, the MccJ25 precursor is processed to yield mature MccJ25, a change in the nucleotide sequence of the mcjA gene ("mutation") can result in a corresponding change in the amino acid sequence of MccJ25 ("substitution"). The relationship between a mutation in the mcjA gene and a corresponding substitution in MccJ25 is determined by, and is predictable from, the universal genetic code.

Introduction of a mutation into the mcjA gene can be accomplished in straightforward fashion by use of molecular-biology and directed-evolution procedures known in the art, including, for example, random mutagenesis, site-directed mutagenesis, and gene synthesis (WO 2004/023093; U.S. application Ser. No. 11/371,736, filed Mar. 9, 2006; Mukhopadhyay, et al. (2004) *Mol. Cell* 14, 739-751; see also Sambrook, J., et al. (1989) *Molecular Cloning: A Laboratory Manual*, Cold Spring Harbor Laboratory, Cold Spring Harbor, N.Y.).

Accordingly, mcjA derivatives containing mutations, and corresponding MccJ25 derivatives containing substitutions, can be, and have been, prepared (WO 2004/023093; U.S. application Ser. No. 11/371,736, filed Mar. 9, 2006; Mukhopadhyay, et al. (2004) *Mol. Cell* 14, 739-751). This approach is limited to production of MccJ25 derivatives containing substitutions at a subset of residue positions, since other residue positions cannot be substituted without disruption of processing or export (U.S. application Ser. No. 11/371,736, filed Mar. 9, 2006). Nevertheless, this approach provides a source of MccJ25 derivatives having different useful properties, including, for example, high affinity for a target of interest, high potency for inhibition of a reaction of interest, or suitability for site-specific incorporation of a detectable group such as a fluorochrome (WO 2004/023093; U.S. application Ser. No. 11/371,736, filed Mar. 9, 2006; Mukhopadhyay, et al. (2004) *Mol. Cell* 14, 739-751).

In the same manner, "libraries" of mcjA derivatives containing single mutations or small numbers of mutations, and corresponding "libraries" of MccJ25 derivatives containing single substitutions or small numbers of substitutions, can be, and have been, prepared (U.S. application Ser. No. 11/371, 736, filed Mar. 9, 2006). This approach is limited to production of libraries of MccJ25 derivatives containing substitutions at a subset of residue positions, since other residue positions cannot be substituted without disruption of processing or export (U.S. application Ser. No. 11/371,736, filed Mar. 9, 2006). Nevertheless, this approach, optionally combined with screening of "libraries" by use of procedures known in the art, provides a further source of MccJ25 derivatives with different useful properties, including, for example, high potency for inhibition of a reaction of interest, or suitability for site-specific incorporation of a detectable group such as a fluorochrome (U.S. application Ser. No. 11/371,736, filed Mar. 9, 2006).

MccJ25 inhibits Gram-negative bacterial RNAP by binding within, and obstructing, the secondary channel of Gram-negative bacterial RNAP (WO 2004/023093; Mukhopadhyay et al. (2004) *Mol. Cell* 14, 739-751; Adelman, et al. (2004) *Mol. Cell* 14, 753-762). Through inhibition of Gram-negative bacterial RNAP, MccJ25 exhibits antibacterial activity against certain Gram-negative bacterial species, including the Gram-negative enterics *Escherchia coli* and *Salmonella* sp. (Delgado, et al. (2001) 183, 4543-4550; Yuzenkova, et al. (2002) 277, 50867-50875). MccJ25 does not inhibit Gram-positive bacterial RNAP or *Thermococcus-Deinococcus* bacterial RNAP, and, accordingly, MccJ25 not inhibit Gram-positive bacterial RNAP or *Thermococcus-Deinococcus* bacterial growth (Yuzenkova, et al. (2002) 277, 50867-50875).

The binding site for MccJ25 within bacterial RNAP is remote from the binding site for rifamycins and from the sites of substitutions that confer resistance to rifamycins (WO 2004/023093; Mukhopadhyay et al. (2004) *Mol. Cell* 14, 739-751; Adelman, et al. (2004) *Mol. Cell* 14, 753-762). Accordingly, MccJ25 exhibits no cross-resistance with rifamycins and retains full ability to inhibit RNAP derivatives resistant to rifamycins.

MccJ25, as a direct consequence of its lariat-peptide/lariat-protoknot structure, exhibits two features useful for drug design and drug discovery:

(1) MccJ25 is genetically encoded (through genetic encoding of a precursor and processing factors; Solbiati, et al. (1996) *J. Bacteriol.* 178, 3661-3663; Solbiati, et al. (1999) *J. Bacteriol.* 181, 2659-2662), permitting efficient production by fermentation (Blond, et al. (1999) *Eur. J. Biochem.* 259, 747-755) and permitting efficient construction of derivatives by molecular-biology or directed-evolution procedures (WO 2004/023093; U.S. application Ser. No. 11/371,736, filed Mar. 9, 2006; Mukhopadhyay, et al. (2004) *Mol. Cell* 14, 739-751).

(2) MccJ25 is resistant to denaturation and proteolysis (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483).

This combination of features is not only useful, but also unusual. Most compounds do not exhibit this combination of features. (Most peptides and proteins exhibit only the first feature. Most non-peptide, non-protein compounds exhibit only the second feature.)

Non-MccJ25-Related Lariat Peptides

We refer herein to compounds according to general structural formula (I) as "non-MccJ25-related lariat peptides."

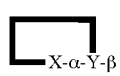

(I)

wherein:
(i) X is an amino acid residue containing a backbone nitrogen atom;
(ii) Y is an amino acid residue containing a side-chain carboxyl group;
(iii) α is a peptide segment of from about 5 to about 8 amino acid residues;
(iv) β is a peptide segment of from about 6 to about 15 amino acid residues;
(v) there is an amide bond between the backbone nitrogen atom of X and the side-chain carboxyl of Y; and
(vi) wherein the compound has less than 25% amino acid sequence identity with microcin J25 (MccJ25).

Non-MccJ25-related lariat peptides are known in the art and include the siamycins [siamycin I (also known as MS-271, NP-06, and FR901724; Yano, et al. (1996) *Bioorg. Med. Chem* 4, 115-120; Katahira, et al. (1996) *Bioorg. Med. Chem* 4, 121-129; Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517), siamycin II (Detlefsen, et al. (1995) *J. Antibiot.* 48, 1515-1517; Constantine, et al. (1995) *J. Biomol. NMR* 5, 271-286), and siamycin III (also known as RP 71955 and aborycin; Helynck, et al. (1993) *J. Antibiot.* 46, 1756-1757; Frechet, et al. (1994) *Biochem.* 33, 42-50; Potterat, et al. (1994) *Liebigs Annalen der Chemie* 7, 741-743)], RES-701-n [RES-701-1 (Yamasaki, et al. (1994) *J. Antibiot.* 47, 276-280; Katahira, et al. (1995) *Bioorg. Med. Chem.* 3, 1273-1280), RES-701-2 (Yano, K. et al. (1995) *J. Antibiot.* 48, 1368-1370; Ogawa, et al. (1995) *J. Antibiot.* 48, 1213-1220), RES-701-3 (Ogawa, et al. (1995) *J. Antibiot.* 48, 1213-1220), and RES-701-4 (Ogawa, et al. (1995) *J. Antibiot.* 48, 1213-1220)], propeptin (Kimura, et al. (1997) *J. Antibiot.* 50, 373-378), anantin (Wyss, et al. (1991) *J. Antibiot.* 44, 172-180), and lariatins [lariatin A and lariatin B (Iwatsuki, et al. (2006) *J. Am. Chem. Soc.* 128, 7486-7491)] (FIG. 4).

Known non-MccJ25-related lariat peptides have lariat-peptide covalent structures similar to the lariat-peptide covalent structure of MccJ25 (Yano, et al. (1996) *Bioorg. Med. Chem* 4, 115-120; Katahira, et al. (1996) *Bioorg. Med. Chem* 4, 121-129; Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517; Constantine, et al. (1995) *J. Biomol. NMR* 5, 271-286; Helynck, et al. (1993) *J. Antibiot.* 46, 1756-1757; Frechet, et al. (1994) *Biochem.* 33, 42-50; Potterat, et al. (1994) *Liebigs Annalen der Chemie* 7, 741-743; Yamasaki, et al. (1994) *J. Antibiot.* 47, 276-280; Katahira, et al. (1995) *Bioorg. Med. Chem.* 3, 1273-1280; Yano, K. et al. (1995) *J. Antibiot.* 48, 1368-1370; Ogawa, et al. (1995) *J. Antibiot.* 48, 1213-1220; Kimura, et al. (1997) *J. Antibiot.* 50, 373-378; Wyss, et al. (1991) *J. Antibiot.* 44, 172-1801; Iwatsuki, et al. (2006) *J. Am. Chem. Soc.* 128, 7486-7491; FIG. 4). The known non-MccJ25-related lariat peptides have lengths of 16-21 residues (FIG. 4). The known non-MccJ25-related lariat peptides contain either: (1) an 8-residue cyclic segment—with a backbone-sidechain amide bond between the backbone nitrogen atom of $Xaa_1$ and the sidechain carboxyl of $Glu_8$ or $Asp_8$-followed by a 9- to 12-residue linear segment; or (2) a 9-residue cyclic segment—with a backbone-sidechain amide bond between the backbone nitrogen atom of $Xaa_1$ and the sidechain carboxyl of $Asp_9$-followed by a 7- to 12-residue linear segment (FIG. 4).

Known non-MccJ25-related lariat peptides have lariat-protoknot three-dimensional structures similar to the lariat-protoknot three-dimensional structure of MccJ25. Three-dimensional structures have been determined for several known non-MccJ25-related lariat peptides, including siamycin I (Katahira, et al. (1996) *Bioorg. Med. Chem* 4, 121-129), siamycin II (Constantine, et al. (1995) *J. Biomol. NMR* 5, 271-286), siamycin III (Frechet, et al. (1994) *Biochem.* 33, 42-50)], RES-701-1 (Katahira, et al. (1995) *Bioorg. Med. Chem.* 3, 1273-1280), and lariatin A (Iwatsuki, et al. (2006) *J. Am. Chem. Soc.* 128, 7486-7491). In each case, the compound has been found to have a lariat-protoknot structure, in which the linear segment of the lariat loops back, and penetrates and threads though the cyclic segment of the lariat (Katahira, et al. (1996) *Bioorg. Med. Chem* 4, 121-129; (Constantine, et al. (1995) *J. Biomol. NMR* 5, 271-286; Frechet, et al. (1994) *Biochem.* 33, 42-50); Katahira, et al. (1995) *Bioorg. Med. Chem.* 3, 1273-1280; Iwatsuki, et al. (2006) *J. Am. Chem. Soc.* 128, 7486-7491).

The known non-MccJ25-related lariat peptides exhibit no significant amino acid similarity to MccJ25 (less than 25% sequence identity; FIG. 4).

The known non-MccJ25-related lariat peptides are produced by bacterial producer strains: *Streptomyces* sp. strains for siamycins, RES-701-n, and anantin (Yano, et al. (1996) *Bioorg. Med. Chem* 4, 115-120; Katahira, et al. (1996) *Bioorg. Med. Chem* 4, 121-129; Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517; Constantine, et al. (1995)

J. Biomol. NMR 5, 271-286; Helynck, et al. (1993) J. Antibiot. 46, 1756-1757; Frechet, et al. (1994) Biochem. 33, 42-50; Potterat, et al. (1994) Liebigs Annalen der Chemie 7, 741-743; Yamasaki, et al. (1994) J. Antibiot. 47, 276-280; Katahira, et al. (1995) Bioorg. Med. Chem. 3, 1273-1280; Yano, K. et al. (1995) J. Antibiot. 48, 1368-1370; Ogawa, et al. (1995) J. Antibiot. 48, 1213-1220; Wyss, et al. (1991) J. Antibiot. 44, 172-1801), a *Microbispora* sp. strain for propeptin (Kimura, et al. (1997) J. Antibiot. 50, 373-378), and a *Rhodococcus* sp. strain for lariatins (Iwatsuki, et al. (2006) J. Am. Chem. Soc. 128, 7486-7491).

It has not been possible to date to re-create the lariat-peptide/lariat-protoknot structure of a non-MccJ25-related lariat peptide without use of the *Streptomyces* sp., *Microbispora* sp. and *Rhodococcus* sp. producer strains. Attempted chemical synthesis of RES-701-1 yields a product having a correct lariat-peptide covalent structure but not having a correct lariat-protoknot three-dimensional structure (i.e., not having the linear segment of the lariat looped back and penetrating and threading through the cyclic segment of the lariat); the resulting material exhibits only 1/700 the biological activity of authentic RES-701-1 (Katahira, et al. (1995) Bioorg. Med. Chem. Lett. 5, 1595-1600; He, et al. (1995) Bioorg. Med. Chem. Lett. 5, 621-626). Chemical synthesis of a linear analog of RES-701-1 yields a product having neither a lariat-peptide covalent structure nor a lariat-protoknot structure; the resulting material exhibits no detectable biological activity (He, et al. (1995) Bioorg. Med. Chem. Lett 5, 621-626). These negative results are reminiscent of negative results obtained for attempted chemical synthesis of MccJ25 and for chemical synthesis and recombinant production of a linear analog of MccJ25 (Rosengren, et al. (2003) J. Am. Chem. Soc. 125, 12464-12474; Wilson, et al. (2003) J. Am. Chem. Soc. 125, 12475-12483)

No lariat-peptide/lariat-protoknot biosynthetic cassette for non-MccJ25-related lariat peptides have been described in prior art.

As a consequence, surrogate-host expression of non-MccJ25-related lariat peptides has not been accomplished in prior art.

As a further consequence, production of substituted derivatives of non-MccJ25-related lariat peptides has not been accomplished in prior art.

As a further consequence, production of libraries of substituted derivatives of non-MccJ25-related lariat peptides has not been accomplished in prior art.

The known non-MccJ25-related lariat peptides have been reported to have useful properties, including antibacterial activity for siamycins (Yano, et al. (1996) Bioorg. Med. Chem. 4, 115-120; Potterat, et al. (1994) Liebigs Annalen der Chemie 7, 741-743), propeptin (Kimura, et al. (1997) J. Antibiot. 50, 373-378), and lariatins (Iwatsuki, et al. (2006) J. Am. Chem. Soc. 128, 7486-7491); antiviral activity for siamycins (Chokekijchai, et al. (1995) Antimicrob. Agents Chemother. 39, 2345-2347; Nakashima, et al. (1996) Biol. Pharm. Bull, 19, 405-412; Detlefsen, et al. (1995) J. Antibiot. 48, 1515-1517; Lin, et al. (1996) Antimicrob. Agents Chemother. 40, 133-138), endothelin type B receptor antagonist activity for RES-701-n (Morishita, et al. (1994) J. Antibiot. 47, 269-275; Ogawa, et al. (1995) J. Antibiot. 48, 1213-1220), prolyl endopeptidase inhibition activity for propeptin (Kimura, et al. (1997) J. Antibiot. 50, 373-378), and atrial natriuretic factor receptor antagonist activity for anantin (Wyss, et al. (1991) J. Antibiot. 44, 172-1801).

The known non-MccJ25-related lariat peptides have not been reported in prior art to inhibit bacterial RNAP.

SUMMARY OF THE INVENTION

This invention provides a method inhibiting a bacterial RNA polymerase with a compound of general structural formula (I):

wherein:

(vii) X is an amino acid residue containing a backbone nitrogen atom;

(viii) Y is an amino acid residue containing a side-chain carboxyl group;

(ix) α is a peptide segment of from about 5 to about 8 amino acid residues;

(x) β is a peptide segment of from about 6 to about 15 amino acid residues;

(xi) there is an amide bond between the backbone nitrogen atom of X and the side-chain carboxyl of Y; and (xii) wherein the compound has less than 25% amino acid sequence identity with microcin J25 (MccJ25).

The compounds of general structural formula (I) inhibit at least one activity of a bacterial RNA polymerase when contacted with a bacterial RNA polymerase.

In a preferred embodiment, X in formula (I) is one of Gly ad Cys, and Y in formula (I) is one of Asp and Glu. In a further preferred embodiment, α in formula (I) is a peptide segment of from 6 to 7 amino acid residues, and β in formula (I) is a peptide segment of from 7 to 14 amino acid residues. In an especially preferred embodiment, at least one amino acid residue of β in formula (I) is threaded through the cycle comprising X-α-Y in formula (I).

The invention has potential applications in control of bacterial RNAP activity, control of bacterial gene expression, control of bacterial growth, antibacterial chemistry, and antibacterial therapy.

BRIEF DESCRIPTION OF THE DRAWINGS

Figure 1:
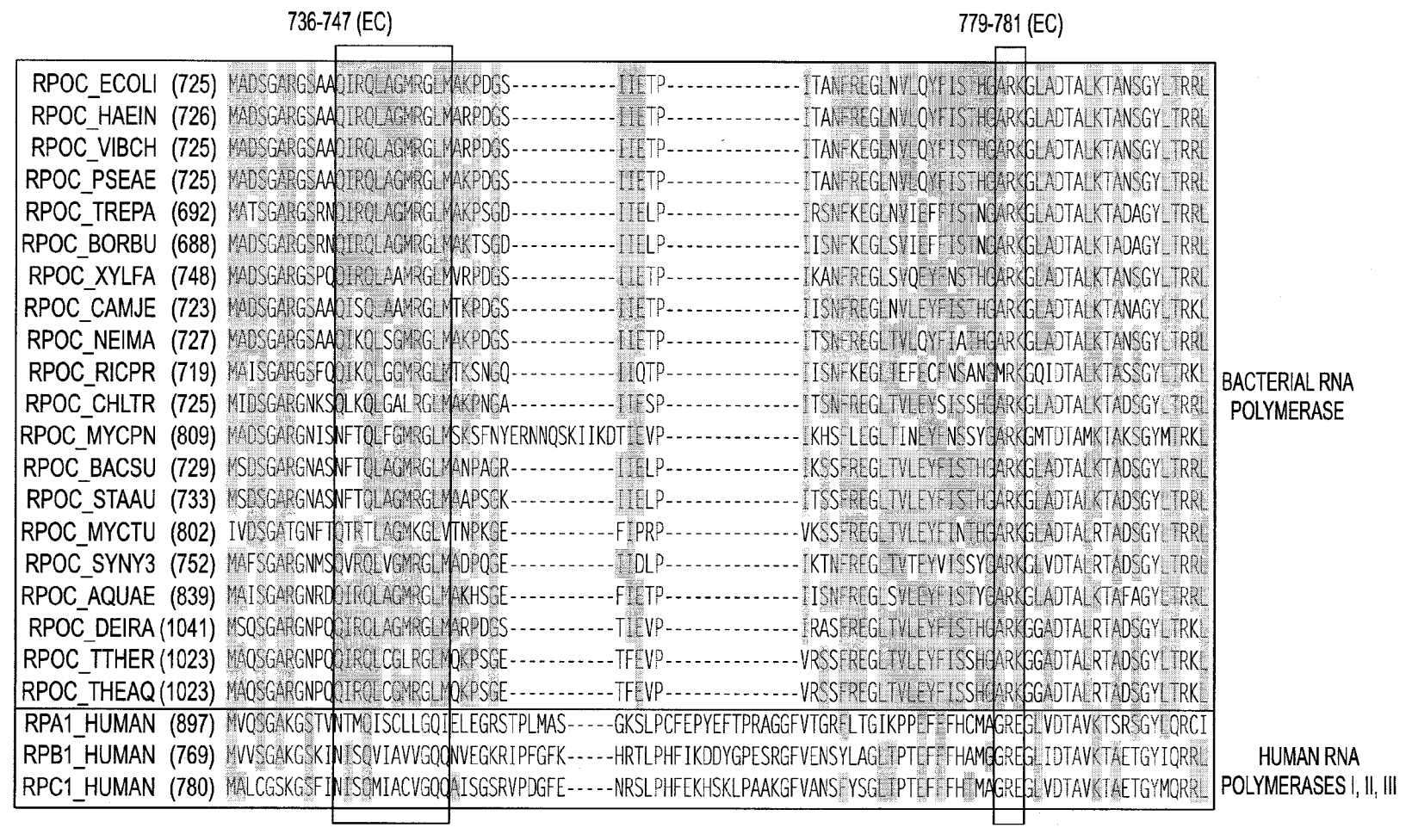

FIG. 1 shows a sequence alignment defining the homologous secondary channel amino acid sequence of bacterial RNAP. The sequence alignment shows amino acid residues 736-747 and 779-781 of the .beta.' subunit of RNAP from *Escherichia coli* (SEQ ID NO. 1); and corresponding residues of the .beta.' subunits of *Haemophilus influenza* (SEQ ID NO. 2), *Vibrio cholera* (SEQ ID NO. 3), *Pseudomonas aeruginose* (SEQ ID NO. 4), *Treponema pallidum* (SEQ ID NO. 5), *Borrelia burgdorferi* (SEQ ID NO. 6), *Xyella fastidiosa* (SEQ ID NO. 7), *Camploacter jejuni* (SEQ ID NO. 8), *Neisseria meningitides* (SEQ ID NO. 9), *Rickettsia prowazekii* (SEQ ID NO. 10), *Chlamydia trachomatis* (SEQ ID NO. 12), *Mycoplasma pneumonia* (SEQ ID NO. 13), *Bacillus subtilis* (SEQ ID NO. 14), *Staphylococcus aureus* (SEQ ID NO. 15), *Mycobacterium tuberculosis* (SEQ ID NO. 16), *Synechocystis* sp. (SEQ ID NO. 17), *Aquifex aeolicus* (SEQ ID NO. 18), *Deinococcus radiodurans* (SEQ ID NO. 19), *Therms thermophiles* (SEQ ID NO. 20), and *Thermus aquaticus* (SEQ ID NO. 21) (collectively, "the homologous secondary channel amino acid sequence"); and corresponding residues of the largest subunits of human RNAP I (SEQ ID NO. 22), RNAP II (SEQ ID NO. 23) and RNAP III (SEQ ID NO. 24).

FIG. 4 shows the lariat-peptide covalent structures of McCJ25 (SEQ ID NO. 26) (Bayro, et al. (2003) J. Am. Chem. Soc. 125, 12382-12383; Rosengren, et al. (2003) J. Am. Chem. Soc. 125, 12464-12474; Wilson, et al. (2003) J. Am. Chem. Soc. 125, 12475-12483) and known non-McCJ25-related lariat peptides [siamycin I (SEQ ID NO. 27) (also known as MS-271, NP-06, and FR901724; Yano, et al. (1996) Bioorg. Med. Chem 4, 115-120; Katahira, et al. (1996) Bioorg. Med. Chem 4, 121-129; Chokekijchai, et al. (1995) Antimicrob. Agents Chemother. 39, 2345-2347; Nakashima, et al. (1996) Biol. Pharm. Bull. 19, 405-412; Detlefsen, et al. (1995) J. Antibiot. 48, 1515-1517), siamycin II (SEQ ID NO. 28) (Detlefsen, et al. (1995) J. Antibiot. 48, 1515-1517; Constantine, et al. (1995) J. Biomol. NMR 5, 271-286), and siamycin III (SEQ ID NO. 29) (also known as RP 71955 and aborycin; Helynck, et al. (1993) J. Antibiot. 46, 1756-1757; Frechet, et al. (1994) Biochem. 33, 42-50; Potterat, et al. (1994) Liebigs Annalen der Chemie 7, 741-743)], RES-701-n [RES-701-1 (SEQ ID NO. 30) (Yamasaki, et al. (1994) J. Antibiot. 47, 276-280; Katahira, et al. (1995) Bioorg. Med. Chem. 3, 1273-1280), RES-701-2 (SEQ ID NO. 31) (Yano, K. et al. (1995) J. Antibiot. 48, 1368-1370; Ogawa, et al. (1995) J. Antibiot. 48, 1213-1220), RES-701-3 (SEQ ID NO. 32) (Ogawa, et al. (1995) J. Antibiot. 48, 1213-1220), and RES-701-4 (SEQ ID NO. 33) (Ogawa, et al. (1995) J. Antibiot. 48, 1213-1220)], propeptin (SEQ ID NO. 34) (Kimura, et al. (1997) J. Antibiot. 50, 373-378), anantin (SEQ ID NO. 35) (Wyss, et al. (1991) J. Antibiot. 44, 172-180), and lariatins [lariatin A (SEQ ID NO. 36) and lariatin B (SEQ ID NO. 37) (Iwatsuki, et al. (2006) J. Am. Chem. Soc. 128, 7486-7491)]. Bold lines indicate backbone-sidechain amide linkages; fine lines indicate sidechain-sidechain disulfide linkages; 7-OH—W denotes 7-hydroxy-tryptophan.

DESCRIPTION OF THE INVENTION

Figures 2A, 2B:
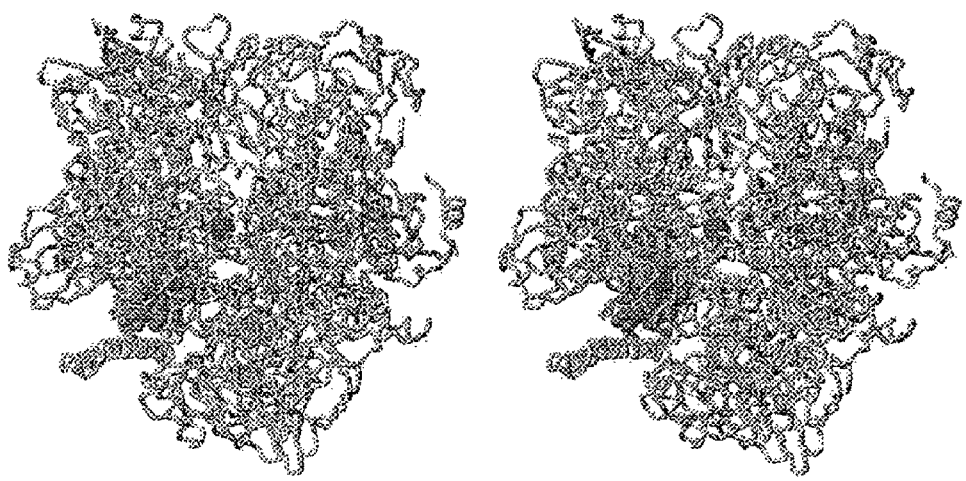
FIGS. 2A and 2B form a stereodiagram that show the position of the homologous secondary channel amino acid sequence within the three-dimensional structure of bacterial RNAP.
Figure 3A:
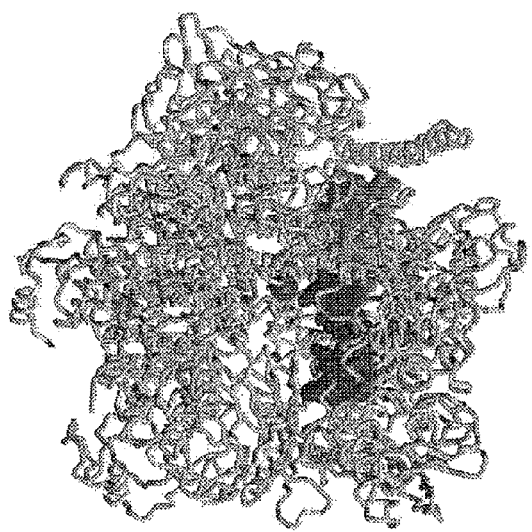
FIGS. 3A and 3B form a stereodiagram that show the relationship between the rifamycin binding site and the homologous secondary channel amino acid sequence within the three-dimensional structure of bacterial RNAP.
Figure 3B:
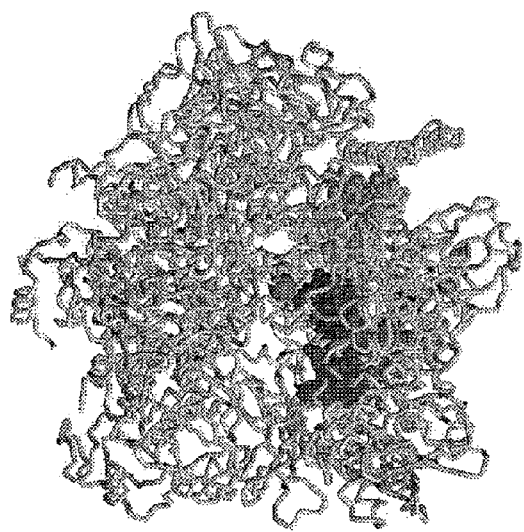
Figure 5:
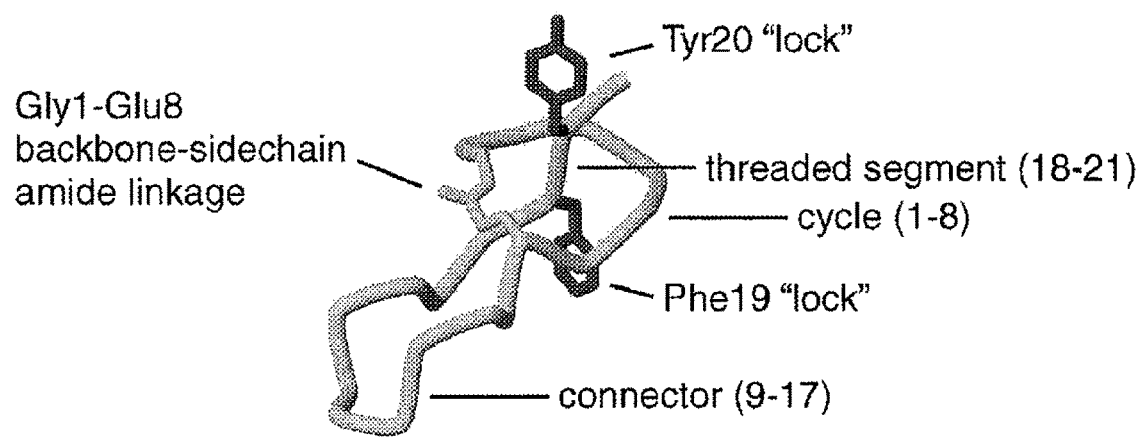
FIG. 5 shows the lariat-protoknot three-dimensional structure of McCJ25 (Bayro, et al. (2003) J. Am. Chem. Soc. 125, 12382-12383; Rosengren, et al. (2003) J. Am. Chem. Soc. 125, 12464-12474; Wilson, et al. (2003) J. Am. Chem. Soc. 125, 12475-12483).

The invention relates to compounds according to general structural formula (I):

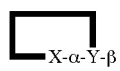

(I)

wherein:
(i) X is an amino acid residue containing a backbone nitrogen atom;
(ii) Y is an amino acid residue containing a side-chain carboxyl group;
(iii) α is a peptide segment of from about 5 to about 8 amino acid residues;
(iv) β is a peptide segment of from about 6 to about 15 amino acid residues;
(v) there is an amide bond between the backbone nitrogen atom of X and the side-chain carboxyl of Y; and
(vi) wherein the compound has less than 25% amino acid sequence identity with MccJ25.

We refer herein to compounds according to general structural formula (I) as "non-MccJ25-related lariat peptides." In a preferred embodiment, X in formula (I) is one of Gly and Cys, and Y in formula (I) is one of Asp and Glu. In a further preferred embodiment, α in formula (I) is a peptide segment of from 6 to 7 amino acid residues, and β in formula (I) is a peptide segment of from 7 to 14 amino acid residues. In an especially preferred embodiment, at least one amino acid residue of β in formula (I) is threaded through the cycle comprising X-α-Y in formula (I).

One aspect of the invention is the finding that non-MccJ25-related lariat peptides are useful as inhibitors of bacterial RNAP. It is disclosed herein that non-MccJ25-related lariat peptides, including, for example, non-MccJ25-related lariat peptides of the siamycin class, non-MccJ25-related lariat peptides of the RES-701-n class, and non-MccJ25-related lariat peptides of the propeptin class, inhibit bacterial RNAP. In particular, it is disclosed herein that the non-MccJ25-related lariat peptides siamycin I, siamycin III, RES-701-1, RES-701-3, and propeptin, inhibit bacterial RNAP.

Another aspect of the invention is the finding that non-MccJ25-related lariat peptides are useful as inhibitors of Gram-negative bacterial RNAP, including, for example, *Escherichia coli* RNAP. It is disclosed herein that non-MccJ25-related lariat peptides, including, for example, siamycin I, siamycin III, RES-701-1, RES-701-3, and propeptin, inhibit Gram-negative bacterial RNAP.

Another aspect of the invention is the finding that non-MccJ25-related lariat peptides are useful as inhibitors of Gram-positive bacterial RNAP, including, for example, *Bacillus subtilis* and *Bacillus cereus* RNAP. It is disclosed herein that non-MccJ25-related lariat peptides siamycin I, siamycin III, RES-701-1, RES-701-3, and propeptin, inhibit Gram-positive bacterial RNAP. This is in contrast to MccJ25, which does not inhibit Gram-positive bacterial RNAP (Yuzenkova, et al. (2002) 277, 50867-50875).

Another aspect of the invention is the finding that non-MccJ25-related lariat peptides, including, for example, siamycin I, siamycin III, RES-701-1, RES-701-3, and propeptin, are useful as inhibitors of *Thermus-Deinoccoccus* bacterial RNAP, including, for example, *Thermus thermophilus* RNAP. It is disclosed herein that non-MccJ25-related lariat peptides siamycin I, siamycin III, RES-701-1, RES-701-3, and propeptin, inhibit *Thermus-Deinoccoccus* bacterial RNAP. This is in contrast to MccJ25, which does not inhibit *Thermus-Deinoccoccus* bacterial RNAP (Yuzenkova, et al. (2002) 277, 50867-50875).

Another aspect of the invention is the finding that non-MccJ25-related lariat peptides, including, for example, siamycin I and siamycin III, RES-701-1, RES-701-3, and propeptin, are useful as broad-spectrum inhibitors of bacterial RNAP, being able to inhibit all three classes of bacterial RNAP: i.e., Gram-negative bacterial RNAP, Gram-positive bacterial RNAP, and *Thermus-Deinoccoccus* bacterial RNAP. This is in contrast to MccJ25, which is a narrow-spectrum inhibitor of bacterial RNAP, being able to inhibit only Gram-negative bacterial RNAP (Yuzenkova, et al. (2002) 277, 50867-50875).

Another aspect of the invention is a method for inhibition of a bacterial RNAP comprising contacting a bacterial RNAP with a non-MccJ25-related lariat peptide, thereby inhibiting at least one activity of the bacterial RNAP. The inhibited activity of the bacterial RNAP may be any detectable activity of the bacterial RNAP. In a preferred embodiment, the inhibited activity of the bacterial RNAP is a functionally important detectable activity of the bacterial RNAP, including, for example, RNA synthesis, DNA binding, DNA unwinding, nucleotide binding, phosphodiester-bond breakage, phosphodiester-bond formation, pyrophosphate release, translocation, initiation-factor binding, elongation-factor binding, and inhibitor binding. In an especially preferred embodiment, the inhibited activity of the bacterial RNAP is RNA synthesis.

Another aspect of the invention is an assay for inhibition of a bacterial RNAP by said method. The assay may entail detection of any detectable activity of a bacterial RNAP. In a preferred embodiment, the assay entails detection of RNA synthesis. In an especially preferred embodiment, the assay is selected from the group comprising an abortive-initiation assay and a run-off transcription assay.

MccJ25, as a direct consequence of its lariat-peptide/lariat-protoknot structure, exhibits two features highly useful for drug design and drug discovery:
  (1) MccJ25 is genetically encoded (through genetic encoding of a precursor and processing factors; Solbiati, et al. (1996) *J. Bacteriol.* 178, 3661-3663; Solbiati, et al. (1999) *J. Bacteriol.* 181, 2659-2662), permitting efficient production by fermentation (Blond, et al. (1999) *Eur. J. Biochem.* 259, 747-755) and permitting efficient construction of derivatives by molecular-biology and directed-evolution methods (WO 2004/023093; U.S. application Ser. No. 11/371,736, filed Mar. 9, 2006; Mukhopadhyay, et al. (2004) *Mol. Cell* 14, 739-751).
  (2) MccJ25 is resistant to denaturation and proteolysis (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483).

This combination of features is not only highly useful, but also highly unusual. Most compounds do not exhibit this combination of features. (Most peptides and proteins exhibit only the first feature. Most non-peptide, non-protein compounds exhibit only the second feature.)

The non-MccJ25-related lariat peptides of this invention, as a direct consequence of their lariat-peptide/lariat-protoknot structures, are expected to exhibit this same highly useful, highly unusual, combination of features.

The invention has applications in control of bacterial RNA polymerase activity, control of bacterial gene expression, control of bacterial growth, antibacterial chemistry, and antibacterial therapy.

EXAMPLES

Example 1

Preparation of Non-MccJ25-Related Lariat Peptides

Example 1-a

Preparation of Siamycin

*Streptomyces* sp. strain SKH-2344 (Chokekijchai, et al. (1995) *Antimicrob. Agents Chemother.* 39, 2345-2347; provided by H. Mitsuya, National Institutes of Health) was cultured as described in Chokekijchai, et al. (1995) *Antimicrob. Agents Chemother.* 39, 2345-2347. Culture broth (8 L) was concentrated to yield a paste, extracted with 2 L methanol (12 h at 22° C.), filtered and concentrated. Mycelia (500 g) were extracted with 2 L methanol (12 h at 22° C.), filtered, and concentrated. The concentrated extract of culture broth and the concentrated extract of mycelia were combined, dissolved in water-saturated butanol, and concentrated. The resulting sample was dissolved in 50 ml 50% methanol and was applied to a preparative C8 cartridge (10 g Mega-BE C8; Varian, Inc.); the cartridge was washed with 50 ml 50% methanol, and eluted successively with 3×10 ml fractions of 60% methanol, 70% methanol and 80% methanol. Fractions containing siamycin I (typically eluted at 70% methanol, detected by molecular mass) were pooled, lyophilized and dissolved in 2 ml 50% methanol. The sample was applied to C18 cartridge (Sep-Pak Vac 12 cc C18-2 g; Waters, Inc). The cartridge was washed with 20 ml 20% acetonitrile and eluted successively with 3×5 ml fractions of 30% acetonitrile, 40% acetonitrile and 50% acetonitrile. Fractions containing siamycin I (typically eluted at 40% acetonitrile, detected by molecular mass) were pooled, lyophilized and dissolved in 1 ml 50% methanol. The sample was further purified by reversed-phase HPLC on a C18, 10 µM, 300 Å column (Phenomenex, Inc.), with solvent A=0.1% trifluoroacetic acid, solvent B=90% actonitrile and 0.1% trifluoroacetic acid, gradient=30-50% solvent B in solvent A in 40 min, and flow rate=2 ml/min. Fractions containing siamycin 1 (retention time ~35 min; detected by UV absorbance at 280 nm) were pooled, lyophilized, re-dissolved in 500 µl 50% methanol, and stored in aliquots at −20° C. Yield was ~5 mg per 1 L culture.

Example 1-b

Preparation of Siamycin III

*Streptomyces griseoflavus* strain Tü 4072 (Potterat, et al. (1994) *Liebigs Annalen der Chemie* 7, 741-743; provided by Combinature Biopharm AG) was cultured as described in Potterat, et al. (1994) *Liebigs Annalen der Chemie* 7, 741-743. 500 g of mycelium (obtained from 8 L culture) was extracted with 2×2 L methanol, filtered, and concentrated to 1 L. The concentrate was extracted with 1 L ethyl acetate and w1 L water-saturated-butanol. The butanolic extract was concentrated to 100 ml under reduced pressure. 20 ml sample was loaded on a Sephadex LH-20 (Amersham Biosciences, Inc) column (2×30 cm). The column was run with methanol at a flow rate 2 ml/min and 10 ml fractions were collected. Fractions containing siamycin III (detected by molecular mass) were lyophilized and dissolved in 20 ml 50% methanol and was applied to a preparative C8 cartridge (10 g Mega-BE C8; Varian, Inc.); the cartridge was washed with 50 ml 50% methanol, and eluted successively with 3×10 ml fractions of 60% methanol, 70% methanol and 80% methanol. Fractions containing siamycin III (typically eluted at 70% methanol, detected by molecular mass) were lyophilized and dissolved in 2 ml 50% methanol. The sample was applied to C18 cartridge (Sep-Pak Vac 3 cc C18-2 g; Waters, Inc). The cartridge was washed with 20% acetonitrile and eluted successively with 3×2 ml fractions of 30% acetonitrile, 40% acetonitrile and 50% acetonitrile. Fractions containing siamycin III (typically eluted at 40% acetonitrile, detected by molecular mass) were pooled, lyophilized, re-dissolved in 250 µl 50% methanol and stored in aliquots at −20° C. Yield was ~20 µg per 1 L culture.

Example 2

Characterization of Non-MccJ25-Related Lariat Peptides

Example 2-a

Inhibition of Bacterial RNA Polymerase by Non-MccJ25-Related Lariat Peptides: Fluorescence-Detected Abortive Initiation Assays Reaction mixtures (51 µl) contained 110 nM bacterial RNAP [*Escherichia coli* $\sigma^{70}$ RNAP holoenzyme (Gram-negative bacterial RNAP; Epicentre, Inc.) or *Thermus thermophilus* $\sigma^A$ RNAP holoenzyme (*Thermus-Deinoccoccus* bacterial RNAP; prepared as in Tuske et al., (2005) *Cell* 122, 541-552)] and lariat peptide [0-250 µM siamycin I (Example 1-a), 0-11 µM siamycin III (Example 1-b), 0-44 µM RES-701-1 (Sigma, Inc.), 0-44 µM RES-701-3 (EMD Biosciences, Inc.), or 0-44 µM propeptin (Kimura, et al. (1997) *J. Antibiot.* 50, 373-378; provided by K.-I. Kimura, Iwate University)] in 50 mM Tris-HCl (pH 8.0), 100 mM KCl (40 mM KCl in experiments with *Thermus. thermophilus* RNAP), 10 mM MgCl$_2$, 1 mM dithiothreitol, 10 µg/ml bovine serum albumin, and 5% glycerol. Following incubation of reaction mixtures for 5 min at 22° C., 1 µl 1.1 µM DNA fragment lacUV5-12 (Mukhopadhyay et al. (2001) *Cell* 106, 453-463) was added. Following further incubation of reaction mixtures for 15 mM at 37° C., 0.5 µl 1 mg/ml heparin (Sigma, Inc.; omitted in experiments with *T. thermophilus* RNAP) and 0.5 µl of 2.75 mM (γ-AmNS)UTP (Molecular Probes, Inc.) were added, and reaction mixtures were transferred to sub-micro fluorometer cuvettes (Starna Cells, Inc.). Following further incubation of reaction mixtures for 2 min at 37° C., RNA synthesis was initiated by addition of 2 µl 11 mM A$_p$A (Sigma, Inc.), and fluorescence emission intensity was monitored for 5 min at 37° C. [excitation wavelength=360 nm and emission wavelength=500 nm; excitation and emission slit widths=4 nm; QuantaMaster QM1 spectrofluorometer (PTI, Inc.)]. The quantity of UMP incorporated into RNA was determined from the quantity of (γ-AmNS) UTP consumed, which, in turn, was calculated as follows (Schlageck et al. 1979):

$$(\gamma\text{-AmNS})\text{UTP}_{consumed} = [(\gamma\text{-AmNS})\text{UTP}_0](F_t - F_0)/(12.4 \times F_0)$$

where (γ-AmNS)UTP$_0$ is the quantity of (γ-AmNS)UTP at time 0, F$_0$ is the fluorescence emission intensity at time 0, and F$_t$ is the fluorescence emission intensity at time t. Normalized data were plotted, and IC$_{50}$ was defined as the concentration of lariat peptide for which transcription inhibition was 50%.

Siamycin I, siamycin III, RES-701-1, RES-701-3, and propeptin were found to inhibit both *Escherichia coli* RNAP (Gram-negative bacterial RNAP) and *Thermus thermophilus* RNAP (*Thermus-Deinococcus* bacterial RNAP), with IC$_{50}$ values in the range of 2-100 µM (Table 1). Siamycin III was found especially potently to inhibit both *Escherichia coli* RNAP (Gram-negative bacterial RNAP) and *Thermus thermophilus* RNAP (*Thermus-Deinococcus* bacterial RNAP), with IC$_{50}$ values of 2 µM and 3 µM, respectively (Table 1).

TABLE 1

Inhibition of bacterial RNA polymerase by non-MccJ25-related lariat peptides: fluorescence-detected abortive initiation assays.

| | IC$_{50}$ (µM) | |
|---|---|---|
| lariat peptide | *Escherichia coli* RNAP | *Thermus thermophilus* RNAP |
| siamycin I | 100 | 100 |
| siamycin III | 3 | 2 |
| RES-701-1 | 30 | 20 |
| RES-701-3 | 20 | 2 |
| propeptin | 30 | 5 |

Example 2-b

Inhibition of Bacterial RNA Polymerase by Non-MccJ25-Related Lariat Peptides: Radioisotope-Detected Abortive Initiation Assays Reaction mixtures (12 µl) contained 60 nM bacterial RNAP [*Escherichia coli* $\sigma^{70}$ RNAP holoenzyme (Gram-negative bacterial RNAP; prepared as in Kuznedelov et al., (2002) *Science* 295, 855-857), *Bacillus subtilis* $\sigma^A$ RNAP holoenzyme (Gram-positive bacterial RNAP; prepared as in Anthony et al., (2000) *Protein Expr Purif.* 19, 350-354), *Bacillus cereus* $\sigma^A$ RNAP holoenzyme (Gram-positive bacterial RNAP; prepared as in Budarina et al., (2004) *Microbiol.* 150, 3691-3701), or *Thermus thermophilus* $\sigma^A$ RNAP holoenzyme (*Thermus-Deinococcus* bacterial RNAP; prepared as in Kuznedelov et al., (2003) *Methods Enzymol.* 370, 94-108)] and lariat peptide [0-50 µM siamycin I (Example 1-a) or 0-10 µM siamycin III (Example 1-b)] in 40 mM Tris-HCl, pH 7.9, 40 mM KCl, and 10 mM MgCl$_2$. Following incubation of reaction mixtures for 5 min at 37° C. (65° C. in experiments with *Thermus thermophilus* RNAP), DNA fragment containing a promoter was added to a final concentration of 20 nM [DNA fragment containing the bacteriophage T7 A1 promoter (Nudler et al., (1995) *Cell* 81, 351-357) in experiments with *Escherichia coli* RNAP and *Thermus thermophilus* RNAP; DNA fragment containing the *Bacillus cereus* hlyII promoter (Budarina et al., (2004) *Microbiol.* 150, 3691-3701) in experiments with *Bacillus cereus* RNAP and *Bacillus subtilis* RNAP]. Following further incubation of reaction mixtures for 15 min at 37° C. (65° C. in experiments with *T. thermophilus* RNAP), transcription was initiated by addition of initiating dinucleotide to a final concentration of 0.5 mM (CpA in experiments with *Escherichia coli* RNAP and *Thermus thermophilus* RNAP; GpA in experiments with *T. thermophilus* RNAP), UTP to the final concentration of 5 µM, and 0.3 µl (3 µCi) [α-P$^{32}$] UTP (3000 Ci/mmol, PerkinElmer Life Sciences, Inc.). Following 5 min at 37° C. (65° C. in experiments with *T. thermophilus* RNAP), reactions were terminated by addition of formamide-containing loading buffer, and reaction products were analyzed by urea-PAGE followed by storage-phosphor imaging (procedures essentially as in Sambrook, J., et al. (1989) *Molecular Cloning: A Laboratory Manual*, Cold Spring Harbor Laboratory, Cold Spring Harbor, N.Y.). Normalized data were plotted, and IC$_{50}$ was defined as the concentration of lariat peptide for which transcription inhibition was 50%.

Siamycin I and siamycin III were found to inhibit *Escherichia coli* RNAP (Gram-negative bacterial RNAP), *Bacillus subtilis* RNAP (Gram-positive bacterial RNAP), and *Bacillus cereus* RNAP (Gram-positive bacterial RNAP), with IC$_{50}$ values in the range of 3-100 µM (Table 2). Siamycin III was found especially potently to inhibit *Escherichia coli* RNAP (Gram-negative bacterial RNAP), *Bacillus subtilis* RNAP (Gram-positive bacterial RNAP), and *Bacillus cereus* RNAP (Gram-positive bacterial RNAP), with $IC_{50}$ values of 3 µM, 3 µM, and 5 µM, respectively (Table 2).

TABLE 2

Inhibition of bacterial RNA polymerase by non-MccJ25-related lariat peptides: radioisotope-detected abortive initiation assays.

| | $IC_{50}$ (µM) | | |
|---|---|---|---|
| lariat peptide | *Escherichia coli* RNAP | *Bacillus subtilis* RNAP | *Bacillus cereus* RNAP |
| siamycin I | 100 | 40 | 40 |
| siamycin III | 3 | 3 | 5 |

Example 2-c

Inhibition of Bacterial RNA Polymerase by Non-MccJ25-Related Lariat Peptides: Radioisotope-Detected Run-Off Transcription Assays Reaction mixtures (12 µl) contained 60 nM bacterial RNAP [*Escherichia coli* $\sigma^{70}$ RNAP holoenzyme (Gram-negative bacterial RNAP; prepared as in Kuznedelov et al., (2002) *Science* 295, 855-857) or *Thermus thermophilus* $\sigma^A$ RNAP holoenzyme (*Thermus-Deinococcus* bacterial RNAP; prepared as in Kuznedelov et al., (2003) *Methods Enzymol.* 370, 94-108)] and 0-10 µM lariat peptide [siamycin III (Example 1-b)] in 40 mM Tris-HCl, pH 7.9, 40 mM KCl, 10 mM $MgCl_2$. Following incubation of reaction mixtures for 5 min at 37° C. (65° C. in experiments with *T. thermophilus* RNAP), DNA fragment containing the T7A1 promoter (Nudler et al., (1995) *Cell* 81, 351-357) was added to final concentration 20 nM. Following further incubation of reaction mixtures for 15 min at 37° C. (65° C. in experiments with *T. thermophilus* RNAP), transcription was initiated by addition CpA to a final concentration of 0.5 mM, ATP to a final concentration of 5 µM, CTP to a final concentration of 5 µM, GTP to a final concentration of 5 µM, UTP to a final concentration of 5 µM, and 0.3 µl (3 µCi) [α-$P^{32}$] UTP (3000 Ci/mmol, PerkinElmer Life Sciences), and transcription was allowed to proceed for 3-5 min at 37° C. (65° C. in experiments with *T. thermophilus* RNAP). Reactions were terminated by addition of formamide-containing loading buffer, and reaction products were resolved by electrophoresis in 10% denaturing gel, followed by storage-phosphor imaging (procedures essentially as in Sambrook, J., et al. (1989) *Molecular Cloning: A Laboratory Manual*, Cold Spring Harbor Laboratory, Cold Spring Harbor, N.Y.). Normalized data were plotted, and $IC_{50}$ was defined as the concentration of lariat peptide for which transcription inhibition was 50%.

Siamycin III was found potently to inhibit both *Escherichia coli* RNAP (Gram-negative bacterial RNAP) and *Thermus thermophilus* RNAP (*Thermus-Deinococcus* bacterial RNAP), with $IC_{50}$ values in the range of 5-6 µM (Table 3).

TABLE 3

Inhibition of bacterial RNA polymerase by non-MccJ25-related lariat peptides: radioisotope-detected run-off transcription assays.

| | $IC_{50}$ (µM) | |
|---|---|---|
| lariat peptide | *Escherichia coli* RNAP | *Thermus thermophilus* RNAP |
| siamycin III | 5 | 6 |

Example 2-d

Inhibition of Bacterial Growth by Non-MccJ25-Related Lariat Peptides

100 µl of a saturated culture of *Escherichia coli* strain D21f2/tolC (Gram-negative bacterium having tolC and rfa mutations, resulting in increased net permeability to small molecules; tolC::Tn10 rfa lac28 proA23 trp30 his51 rpsL173 ampC tsx81; Fralick, et al. (1994) *J. Bacteriol.* 176, 6404-6406), *Escherichia coli* strain DH5α (Gram-negative bacterium; φ80dlacZΔM15, Δ(lacZYA-argF)U169, deoR, recA1, endA1, hsdR17 (rk⁻, mk⁺), phoA, supE44, λ⁻, thi-I, gyrA96, relA1 Invitrogen, Inc.), *Bacillus subtilis* strain MH5636 (Gram-positive bacterium; pheA1 trpC2 rpoC::Hisx10 Cm; Qi, et al., (1998) *Mol. Microbiol.* 28, 1187-1197), and *Bacillus cereus* strain VKM-B771 (Gram-positive bacterium; Budarina et al., (2004) *Microbiol.* 150, 3691-370) in LB (Sambrook, J., et al. (1989) *Molecular Cloning: A Laboratory Manual*, Cold Spring Harbor Laboratory, Cold Spring Harbor, N.Y.) was added to 3.5 ml pre-melted top-agar (Sambrook, I., et al. (1989) *Molecular Cloning: A Laboratory Manual*, Cold Spring Harbor Laboratory, Cold Spring Harbor, N.Y.) pre-equilibrated at 45° C. The mixture was spread on a LB-agar plate (Sambrook, J., et al. (1989) *Molecular Cloning: A Laboratory Manual*, Cold Spring Harbor Laboratory, Cold Spring Harbor, N.Y.), allowed to equilibrate for 30 min at 22° C., and then spotted with 2.5 µl aliquots of 6.25, 12.5, 25, 50, 100 µM siamycin I (Example 1-a), or 6.25, 12.5, 25, 50, and 100 µM siamycin III (Example 1-b), in 50% methanol. Plates were incubated 10 h at 37° C., and cell growth was monitored. The minimal inhibitory concentration (MIC) was defined as the lowest concentration of lariat peptide for which inhibition of bacterial growth was observed.

Siamycin I and siamycin III were found to inhibit growth of *Escherichia coli* strain D21f2/tolC (Gram-negative bacterium having to/C and rfa mutations, resulting in increased net permeability to small molecules), *Bacillus subtilis* strain MH5636 (Gram-positive bacterium), and *Bacillus cereus* strain VKM-B771 (Gram-positive bacterium), with MIC values of 25 µM, 50 µM, and 50 µM, respectively (Table 4). Siamycin I and siamycin III were found not detectably to inhibit growth of *Escherichia coli* strain DH5α (Gram-negative bacterium not having tolC and yfa mutations) (MIC>100 µM; Table 4).

TABLE 4

Inhibition of bacterial growth by non-MccJ25-related lariat peptides: solid-medium assays.

| | MIC (µM) | | | |
|---|---|---|---|---|
| lariat peptide | *Escherichia coli* strain D21f2/tolC | *Escherichia coli* strain DH5α | *Bacillus subtilis* strain MH5636 | *Bacillus cereus* strain VKM-B771 |
| siamycin I | 25 | >1600 | 50 | 50 |
| siamycin III | 25 | >100 | 50 | 50 |

The invention claimed is:

1. A method of inhibiting a Gram-negative bacterial RNA polymerase comprising:
   (a) providing a lariat peptide of formula (I):

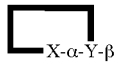 (I)

wherein:
   (i) X is an amino acid residue containing a backbone nitrogen atom;
   (ii) Y is an amino acid residue containing a side-chain carboxyl group;
   (iii) α is a peptide segment of from about 5 to about 8 amino acid residues;
   (iv) β is a peptide segment of from about 6 to about 15 amino acid residues;
   (v) there is an amide bond between the backbone nitrogen atom of X and the side-chain carboxyl of Y; and
   (vi) wherein the lariat peptide has less than 25% amino acid sequence identity with microcin J25 (MccJ25); and
   b) contacting a Gram-negative bacterial RNA polymerase with the lariat peptide of formula (I), thereby inhibiting RNA synthesis activity of the Gram-negative bacterial RNA polymerase, wherein the lariat peptide of formula (I) is selected from the group consisting of RES-701-1, RES-701-2, RES-701-3 and RES-701-4.

2. The method of claim 1, wherein the Gram-negative bacterial RNA polymerase is selected from the group consisting of *Escherichia coli* RNA polymerase and *Thermus thermophiles* RNA polymerase.

3. The method of claim 1, wherein the Gram-negative bacterial RNA polymerase is a RNA polymerase holoenzyme.

4. The method of claim 1, wherein the Gram-negative bacterial RNA polymerase is a bacteria RNA polymerase core enzyme.

5. The method of claim 1, further comprising measuring an effect of the lariat peptide of formula (I) on an activity of a bacterial RNA polymerase.

6. The method of claim 1, further comprising measuring an effect of the lariat peptide of formula (I) on growth of a bacterium.

7. The method of claim 6, wherein the bacterium is selected from the group consisting of a Gram-negative bacterium and a Gram-positive bacterium.

8. The method of claim 7, wherein the Gram-negative bacterium is *Escherichia coli*.

9. The method of claim 8, wherein the bacterium is a strain of *Escherichia coli* having a tolC mutation.

10. The method of claim 9, wherein the bacterium is a strain of *Escherichia coli* having a tolC mutation and an rfa mutation.

11. The method of claim 7, wherein the Gram-positive bacterium is *Bacillus* sp.

12. The method of claim 11, wherein the *Bacillus* sp, is selected from the group consisting of *Bacillus subtilis* and *Bacillus cereus*.

13. A method of inhibiting an isolated bacterial Gram-negative RNA polymerase comprising:
   (a) providing a lariat peptide of formula (I):

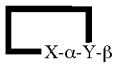

(I)

wherein:
   (i) X is an amino acid residue containing a backbone nitrogen atom;
   (ii) Y is an amino acid residue containing a side-chain carboxyl group;
   (iii) α is a peptide segment of from about 5 to about 8 amino acid residues;
   (iv) β is a peptide segment of from about 6 to about 15 amino acid residues;
   (v) there is an amide bond between the backbone nitrogen atom of X and the side-chain carboxyl of Y; and
   (vi) wherein the lariat peptide has less than 25% amino acid sequence identity with microcin J25 (MccJ25); and
   b) contacting an isolated Gram-negative bacterial RNA polymerase with the lariat peptide of formula (I), thereby inhibiting RNA synthesis activity of the isolated Gram-negative bacterial RNA polymerase, wherein the lariat peptide of formula (I) is propeptin.

14. The method of claim 13, wherein the isolated Gram-negative bacterial RNA polymerase is selected from the group consisting of *Escherichia coli* RNA polymerase and *Thermus thermophilus* RNA polymerase.

15. The method of claim 13, wherein the isolated Gram-negative bacterial RNA polymerase is a bacteria RNA polymerase holoenzyme.

16. The method of claim 13, wherein the isolated Gram-negative bacterial RNA polymerase is a bacteria RNA polymerase core enzyme.

17. The method of claim 13, further comprising measuring an effect of propeptin on an activity of a bacterial RNA polymerase.

18. The method of claim 13, further comprising measuring an effect of the lariat peptide of formula (I) on growth of a bacterium.

19. The method of claim 18, wherein the bacterium is selected from the group consisting of a Gram-negative bacterium and a Gram-positive bacterium.

20. The method of claim 19, wherein the Gram-negative bacterium is *Escherichia coli*.

21. The method of claim 20, wherein the bacterium is a strain of *Escherichia coli* having a tolC mutation.

22. The method of claim 21, wherein the bacterium is a strain of *Escherichia coli* having a tolC mutation and an rfa mutation.

23. The method of claim 19, wherein the Gram-positive bacterium is *Bacillus* sp.

24. The method of claim 23, wherein the *Bacillus* sp, is selected from the group consisting of *Bacillus subtilis* and *Bacillus cereus*.

25. A method of inhibiting an isolated bacterial RNA polymerase comprising:
   (a) providing a lariat peptide of formula (I):

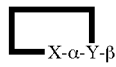

(I)

wherein:
   (i) X is an amino acid residue containing a backbone nitrogen atom;
   (ii) Y is an amino acid residue containing a side-chain carboxyl group;
   (iii) α is a peptide segment of from about 5 to about 8 amino acid residues;
   (iv) β is a peptide segment of from about 6 to about 15 amino acid residues;
   (v) there is an amide bond between flue backbone nitrogen atom of X and the side-chain carboxyl of Y; and
   (vi) wherein the lariat peptide has less than 25% amino acid sequence identity with microcin J25 (MccJ25); and
   b) contacting an isolated bacterial RNA polymerase with the lariat peptide compound of formula (I), thereby inhibiting RNA synthesis activity of the isolated bacterial RNA polymerase, wherein the lariat peptide of formula (I) is selected from the group consisting of siamycin I, siamycin II and siamycin III.

26. The method of claim 25, wherein the isolated bacterial RNA polymerase is a Gram-negative bacterial RNA polymerase.

27. The method of claim 26, wherein the Gram-negative bacterial RNA polymerase is selected from the group consisting of *Escherichia coli* RNA polymerase and *Thermus thermophilus* RNA polymerase.

28. The method of claim 25, wherein the isolated bacterial RNA polymerase is a Gram-positive bacterial RNA polymerase.

29. The method of claim 28, wherein the Gram-positive bacterial polymerase is selected from the group consisting of *Bacillus subtilis* RNA polymerase and *Bacillus cereus* RNA polymerase.

30. The method of claim 25, wherein the isolated bacterial RNA polymerase is a bacterial RNA polymerase holoenzyme.

31. The method of claim 25, wherein the isolated bacterial RNA polymerase is a bacterial RNA polymerase core enzyme.

32. The method of claim 25, further comprising the step of measuring an effect of the lariat peptide of formula (I) on an activity of a further bacterial RNA polymerase.

33. The method of claim 25, further comprising measuring an effect of the lariat peptide of formula (I) on growth of a bacterium.

34. The method of claim 33, wherein the bacterium is selected from the group consisting of a Gram-negative bacterium and a Gram-positive bacterium.

35. The method of claim 34, wherein the bacterium is *Escherichia coli*.

36. The method of claim 35, wherein the bacterium is a strain of *Escherichia coli* having a tolC mutation.

37. The method of claim 36, wherein the bacterium is a strain of *Escherichia coli* having a tolC mutation and an rfa mutation.

38. The method of claim 34, wherein the Gram-positive bacterium is *Bacillus* sp.

39. The method of claim 38, wherein the *Bacillus* sp, is selected from the group consisting of *Bacillus subtilis* and *Bacillus cereus*.

* * * * *